(12) United States Patent
Ross

(10) Patent No.: US 10,390,732 B2
(45) Date of Patent: Aug. 27, 2019

(54) BREATH ANALYZER, SYSTEM, AND COMPUTER PROGRAM FOR AUTHENTICATING, PRESERVING, AND PRESENTING BREATH ANALYSIS DATA

(71) Applicant: Digital Ally, Inc., Lenexa, KS (US)

(72) Inventor: Stanton E. Ross, Overland Park, KS (US)

(73) Assignee: Digital Ally, Inc., Lenexa, KS (US)

( * ) Notice: Subject to any disclaimer, the term of this patent is extended or adjusted under 35 U.S.C. 154(b) by 0 days.

(21) Appl. No.: 14/517,160

(22) Filed: Oct. 17, 2014

(65) Prior Publication Data

US 2015/0051502 A1 Feb. 19, 2015

Related U.S. Application Data

(63) Continuation-in-part of application No. 13/967,151, filed on Aug. 14, 2013, now Pat. No. 9,253,452.

(51) Int. Cl.
*A61B 5/08* (2006.01)
*A61B 5/00* (2006.01)
(Continued)

(52) U.S. Cl.
CPC ............ *A61B 5/082* (2013.01); *A61B 5/0004* (2013.01); *A61B 5/097* (2013.01); *A61B 5/1176* (2013.01);
(Continued)

(58) Field of Classification Search
USPC .......................................................... 600/532
See application file for complete search history.

(56) References Cited

U.S. PATENT DOCUMENTS 4,409,670 A 10/1983 Herndon et al.
4,789,904 A 12/1988 Peterson
(Continued)

FOREIGN PATENT DOCUMENTS

DE 102010019451 A1 11/2011
EP 2479993 A2 7/2012
(Continued)

OTHER PUBLICATIONS

File History of U.S. Appl. No. 14/040,329, filed Sep. 27, 2013, entitled Portable Video and Imaging System; Applicant: Digital Ally, Inc.
(Continued)

*Primary Examiner* — Michael R Bloch
(74) *Attorney, Agent, or Firm* — Erise IP, P.A

(57) ABSTRACT

A breath analyzer, a system, and a computer program for administering a breath analysis to a donor and recording a breath analysis result. Embodiments of the invention authenticate that the breath analysis was performed correctly, preserves the breath analysis results by communicating with other devices, and presents the breath analysis results by superimposing them on recorded video data. The breath analyzer includes a breath receptor for receiving a breath sample from the donor, an analyzing element for determining a breath analysis result, a communications element for sending information indicative of the breath analysis result to a recording device manager, and a housing for securing the components in a handheld device. The system comprises the breath analyzer, a recording device manager for synchronizing the recordings, and at least one ancillary camera for recording the breath analysis.

23 Claims, 9 Drawing Sheets

(51) Int. Cl.

| | | |
|---|---|---|
| *A61B 5/1171* | (2016.01) | |
| *A61B 5/097* | (2006.01) | |
| *A61B 5/18* | (2006.01) | |
| *H04N 5/77* | (2006.01) | |
| *H04N 9/82* | (2006.01) | |
| *A61B 90/00* | (2016.01) | |
| *A61B 90/90* | (2016.01) | |
| *A61B 90/98* | (2016.01) | |

(52) U.S. Cl.
CPC ............... *A61B 5/18* (2013.01); *A61B 5/742* (2013.01); *A61B 90/361* (2016.02); *A61B 90/90* (2016.02); *A61B 90/98* (2016.02); *H04N 5/772* (2013.01); *H04N 9/8205* (2013.01)

(56) References Cited

U.S. PATENT DOCUMENTS

| | | |
|---|---|---|
| 4,863,130 A | 9/1989 | Marks, Jr. |
| 4,918,473 A | 4/1990 | Blackshear |
| 5,027,104 A | 6/1991 | Reid |
| 5,096,287 A | 3/1992 | Kakinami et al. |
| 5,111,289 A | 5/1992 | Lucas et al. |
| 5,289,321 A | 2/1994 | Secor |
| 5,381,155 A | 1/1995 | Gerber |
| 5,408,330 A | 4/1995 | Squicciarii et al. |
| 5,446,659 A | 8/1995 | Yamawaki |
| 5,453,939 A | 9/1995 | Hoffman et al. |
| 5,473,729 A | 12/1995 | Bryant et al. |
| 5,479,149 A | 12/1995 | Pike |
| 5,497,419 A | 3/1996 | Hill |
| 5,526,133 A | 6/1996 | Paff |
| 5,585,798 A | 12/1996 | Yoshioka et al. |
| 5,642,285 A | 6/1997 | Woo et al. |
| 5,668,675 A | 9/1997 | Fredricks |
| 5,689,442 A | 11/1997 | Swanson et al. |
| 5,742,336 A | 4/1998 | Lee |
| 5,752,632 A | 5/1998 | Sanderson et al. |
| 5,798,458 A | 8/1998 | Monroe |
| 5,815,093 A | 9/1998 | Kikinis |
| 5,850,613 A | 12/1998 | Bullecks |
| 5,878,283 A | 3/1999 | House et al. |
| 5,886,739 A | 3/1999 | Winningstad |
| 5,890,079 A | 3/1999 | Levine |
| 5,926,210 A | 7/1999 | Hackett et al. |
| 5,962,806 A | 10/1999 | Coakley et al. |
| 5,978,017 A | 11/1999 | Tino |
| 5,983,161 A | 11/1999 | Lemelson et al. |
| 5,996,023 A | 11/1999 | Winter et al. |
| 6,008,841 A | 12/1999 | Charlson |
| 6,028,528 A | 2/2000 | Lorenzetti et al. |
| 6,052,068 A | 4/2000 | Price R-W et al. |
| 6,097,429 A | 8/2000 | Seeley et al. |
| 6,100,806 A | 8/2000 | Gaukel |
| 6,121,881 A | 9/2000 | Bieback et al. |
| 6,141,609 A | 10/2000 | Herdeg et al. |
| 6,141,611 A | 10/2000 | Mackey et al. |
| 6,163,338 A | 12/2000 | Johnson et al. |
| 6,175,300 B1 | 1/2001 | Kendrick |
| 6,298,290 B1 | 10/2001 | Abe et al. |
| 6,310,541 B1 | 10/2001 | Atkins |
| 6,314,364 B1 | 11/2001 | Nakamura |
| 6,324,053 B1 | 11/2001 | Kamijo |
| 6,326,900 B2 | 12/2001 | DeLine et al. |
| 6,333,694 B2 | 12/2001 | Pierce et al. |
| 6,333,759 B1 | 12/2001 | Mazzilli |
| 6,370,475 B1 | 4/2002 | Breed et al. |
| RE37,709 E | 5/2002 | Dukek |
| 6,389,340 B1 | 5/2002 | Rayner |
| 6,396,403 B1 | 5/2002 | Haner |
| 6,405,112 B1 | 6/2002 | Rayner |
| 6,449,540 B1 | 9/2002 | Rayner |
| 6,452,572 B1 | 9/2002 | Fan et al. |
| 6,490,409 B1 | 12/2002 | Walker |
| 6,518,881 B2 | 2/2003 | Monroe |
| 6,525,672 B2 | 2/2003 | Chainer et al. |
| 6,546,119 B2 | 4/2003 | Ciolli et al. |
| 6,560,463 B1 | 5/2003 | Santhoff |
| 6,563,532 B1 | 5/2003 | Strub et al. |
| 6,591,242 B1 | 7/2003 | Karp et al. |
| 6,681,195 B1 | 1/2004 | Poland et al. |
| 6,690,268 B2 | 2/2004 | Schofield et al. |
| 6,697,103 B1 | 2/2004 | Fernandez et al. |
| 6,718,239 B2 | 4/2004 | Rayner |
| 6,727,816 B1 | 4/2004 | Helgeson |
| 6,748,792 B1 | 6/2004 | Freund et al. |
| 6,823,621 B2 | 11/2004 | Gotfried |
| 6,831,556 B1 | 12/2004 | Boykin |
| 6,856,873 B2 | 2/2005 | Breed et al. |
| 6,883,694 B2 | 4/2005 | Abelow |
| 6,970,183 B1 | 11/2005 | Monroe |
| 7,012,632 B2 | 3/2006 | Freeman et al. |
| 7,034,683 B2 | 4/2006 | Ghazarian |
| D520,738 S | 5/2006 | Tarantino |
| 7,038,590 B2 | 5/2006 | Hoffman et al. |
| 7,071,969 B1 | 7/2006 | Stimson, III |
| 7,088,387 B1 | 8/2006 | Freeman et al. |
| D529,528 S | 10/2006 | Ross, Jr. et al. |
| 7,119,832 B2 | 10/2006 | Blanco et al. |
| 7,126,472 B2 | 10/2006 | Kraus et al. |
| 7,147,155 B2 | 12/2006 | Weekes |
| 7,180,407 B1 | 2/2007 | Guo et al. |
| 7,190,882 B2 | 3/2007 | Gammenthaler |
| 7,359,553 B1 | 4/2008 | Wendt et al. |
| 7,363,742 B2 | 4/2008 | Nerheim |
| 7,371,021 B2 | 5/2008 | Ross, Jr. et al. |
| 7,421,024 B2 | 9/2008 | Castillo |
| 7,436,143 B2 | 10/2008 | Lakshmanan et al. |
| 7,436,955 B2 | 10/2008 | Yan et al. |
| 7,448,996 B2 | 11/2008 | Khanuja et al. |
| 7,456,875 B2 | 11/2008 | Kashiwa |
| 7,488,996 B2 | 2/2009 | Chang |
| 7,496,140 B2 | 2/2009 | Winningstad et al. |
| 7,500,794 B1 | 3/2009 | Clark |
| 7,508,941 B1 | 3/2009 | O'Toole, Jr. et al. |
| 7,536,457 B2 | 5/2009 | Miller |
| 7,539,533 B2 | 5/2009 | Tran |
| 7,561,037 B1 | 7/2009 | Monroe |
| 7,594,305 B2 | 9/2009 | Moore |
| 7,602,301 B1 | 10/2009 | Stirling et al. |
| 7,656,439 B1 | 2/2010 | Manico et al. |
| 7,659,827 B2 | 2/2010 | Gunderson et al. |
| 7,680,947 B2 | 3/2010 | Nicholl et al. |
| 7,697,035 B1 | 4/2010 | Suber, III et al. |
| 7,804,426 B2 | 9/2010 | Etcheson |
| 7,806,525 B2 | 10/2010 | Howell et al. |
| 7,853,944 B2 | 12/2010 | Choe |
| 7,944,676 B2 | 5/2011 | Smith et al. |
| 8,077,029 B1 | 12/2011 | Daniel et al. |
| 8,121,306 B2 | 2/2012 | Cilia et al. |
| 8,175,314 B1 | 5/2012 | Webster |
| 8,269,617 B2 | 9/2012 | Cook et al. |
| 8,314,708 B2 | 11/2012 | Gunderson et al. |
| 8,350,907 B1 | 1/2013 | Blanco et al. |
| 8,356,438 B2 | 1/2013 | Brundula et al. |
| 8,373,567 B2 | 2/2013 | Denson |
| 8,373,797 B2 * | 2/2013 | Ishii ................... H04N 19/112 348/445 |
| 8,384,539 B2 | 2/2013 | Denny et al. |
| 8,446,469 B2 | 5/2013 | Blanco et al. |
| 8,456,293 B1 | 6/2013 | Trundle et al. |
| 8,503,972 B2 | 8/2013 | Haler et al. |
| 8,508,353 B2 | 8/2013 | Cook et al. |
| 8,520,069 B2 | 8/2013 | Haler |
| 8,594,485 B2 | 11/2013 | Brundula |
| 8,606,492 B1 | 12/2013 | Botnen |
| 8,676,428 B2 | 3/2014 | Richardson et al. |
| 8,690,365 B1 | 4/2014 | Williams |
| 8,707,758 B2 | 4/2014 | Keays |
| 8,725,462 B2 | 5/2014 | Jain et al. |
| 8,744,642 B2 | 6/2014 | Nemat-Nasser et al. |
| 8,780,205 B2 | 7/2014 | Boutell et al. |
| 8,781,292 B1 | 7/2014 | Ross et al. |

(56) References Cited

U.S. PATENT DOCUMENTS

| | | |
|---|---|---|
| 8,805,431 B2 | 8/2014 | Vasavada et al. |
| 8,849,501 B2 | 9/2014 | Cook et al. |
| 8,854,199 B2 | 10/2014 | Cook et al. |
| 8,887,208 B1 | 11/2014 | Merrit et al. |
| 8,890,954 B2 | 11/2014 | O'Donnell et al. |
| 8,896,694 B2 | 11/2014 | O'Donnell et al. |
| 8,930,072 B1 | 1/2015 | Lambert et al. |
| 8,934,045 B2 | 1/2015 | Karn et al. |
| 8,989,914 B1 | 3/2015 | Nemat-Nasser et al. |
| 8,996,234 B1 | 3/2015 | Tamari et al. |
| 8,996,240 B2 | 3/2015 | Plante |
| 9,002,313 B2 | 4/2015 | Sink et al. |
| 9,003,474 B1 | 4/2015 | Smith |
| 9,058,499 B1 | 6/2015 | Smith |
| 9,122,082 B2 | 9/2015 | Abreau |
| 9,123,241 B2 | 9/2015 | Grigsby et al. |
| 9,164,543 B2 | 10/2015 | Minn et al. |
| 9,591,255 B2 | 3/2017 | Sakiewica et al. |
| 9,728,228 B2 | 8/2017 | Palmer et al. |
| 2001/0033661 A1 | 10/2001 | Prokoski |
| 2002/0013517 A1 | 1/2002 | West et al. |
| 2002/0019696 A1 | 2/2002 | Kruse |
| 2002/0032510 A1 | 3/2002 | Turnball et al. |
| 2002/0044065 A1 | 4/2002 | Quist et al. |
| 2002/0049881 A1 | 4/2002 | Sugimura |
| 2002/0084130 A1* | 7/2002 | Der Ghazarian et al. .... 180/272 |
| 2002/0131768 A1 | 9/2002 | Gammenthaler |
| 2002/0135336 A1 | 9/2002 | Zhou et al. |
| 2002/0159434 A1 | 10/2002 | Gosior et al. |
| 2002/0191952 A1 | 12/2002 | Fiore et al. |
| 2003/0040917 A1 | 2/2003 | Fiedler |
| 2003/0080878 A1 | 5/2003 | Kirmuss |
| 2003/0081121 A1 | 5/2003 | Kirmuss |
| 2003/0081934 A1 | 5/2003 | Kirmuss |
| 2003/0081935 A1* | 5/2003 | Kirmuss ................ 386/46 |
| 2003/0081942 A1 | 5/2003 | Melnyk et al. |
| 2003/0095688 A1 | 5/2003 | Kirmuss |
| 2003/0106917 A1 | 6/2003 | Shelter et al. |
| 2003/0133018 A1 | 7/2003 | Ziemkowski |
| 2003/0151510 A1 | 8/2003 | Quintana et al. |
| 2003/0173408 A1 | 9/2003 | Mosher, Jr. et al. |
| 2003/0184674 A1 | 10/2003 | Manico et al. |
| 2003/0185417 A1 | 10/2003 | Alattar et al. |
| 2003/0215010 A1 | 11/2003 | Kashiwa |
| 2003/0215114 A1 | 11/2003 | Kyle |
| 2003/0222982 A1 | 12/2003 | Hamdan et al. |
| 2004/0008255 A1 | 1/2004 | Lewellen |
| 2004/0043765 A1 | 3/2004 | Tolhurst |
| 2004/0143373 A1 | 6/2004 | Ennis |
| 2004/0145457 A1 | 7/2004 | Schofield et al. |
| 2004/0150717 A1 | 8/2004 | Page et al. |
| 2004/0168002 A1 | 8/2004 | Accarie et al. |
| 2004/0199785 A1 | 10/2004 | Pederson |
| 2004/0223054 A1 | 11/2004 | Rotholtz |
| 2004/0243734 A1 | 12/2004 | Kitagawa et al. |
| 2004/0267419 A1 | 12/2004 | Jeng |
| 2005/0030151 A1 | 2/2005 | Singh |
| 2005/0035161 A1 | 2/2005 | Shioda |
| 2005/0046583 A1 | 3/2005 | Richards |
| 2005/0050266 A1 | 3/2005 | Haas et al. |
| 2005/0068169 A1 | 3/2005 | Copley et al. |
| 2005/0068417 A1 | 3/2005 | Kreiner et al. |
| 2005/0083404 A1 | 4/2005 | Pierce et al. |
| 2005/0094966 A1 | 5/2005 | Elberbaum |
| 2005/0100329 A1 | 5/2005 | Lao et al. |
| 2005/0101334 A1 | 5/2005 | Brown et al. |
| 2005/0132200 A1 | 6/2005 | Jaffe et al. |
| 2005/0134966 A1 | 6/2005 | Burgner |
| 2005/0151852 A1 | 7/2005 | Jomppanen |
| 2005/0167172 A1 | 8/2005 | Fernandez |
| 2005/0185438 A1 | 8/2005 | Ching |
| 2005/0206532 A1 | 9/2005 | Lock |
| 2005/0206741 A1 | 9/2005 | Raber |
| 2005/0228234 A1 | 10/2005 | Yang |
| 2005/0232469 A1 | 10/2005 | Schofield et al. |
| 2005/0243171 A1 | 11/2005 | Ross, Sr. et al. |
| 2005/0258942 A1 | 11/2005 | Manasseh et al. |
| 2006/0009238 A1 | 1/2006 | Stanco et al. |
| 2006/0028811 A1 | 2/2006 | Ross, Jr. et al. |
| 2006/0055786 A1 | 3/2006 | Olilla |
| 2006/0082730 A1 | 4/2006 | Franks |
| 2006/0158968 A1 | 7/2006 | Vanman et al. |
| 2006/0164220 A1 | 7/2006 | Harter, Jr. et al. |
| 2006/0164534 A1 | 7/2006 | Robinson et al. |
| 2006/0170770 A1 | 8/2006 | MacCarthy |
| 2006/0176149 A1 | 8/2006 | Douglas |
| 2006/0183505 A1 | 8/2006 | Willrich |
| 2006/0193749 A1 | 8/2006 | Ghazarian et al. |
| 2006/0203090 A1 | 9/2006 | Wang et al. |
| 2006/0220826 A1 | 10/2006 | Rast |
| 2006/0225253 A1 | 10/2006 | Bates |
| 2006/0244601 A1 | 11/2006 | Nishimura |
| 2006/0256822 A1 | 11/2006 | Kwong et al. |
| 2006/0267773 A1* | 11/2006 | Roque .............. G06K 19/07728 340/572.7 |
| 2006/0270465 A1 | 11/2006 | Lee et al. |
| 2006/0271287 A1 | 11/2006 | Gold et al. |
| 2006/0274166 A1 | 12/2006 | Lee et al. |
| 2006/0274828 A1 | 12/2006 | Siemens et al. |
| 2006/0276200 A1 | 12/2006 | Radhakrishnan et al. |
| 2006/0282021 A1 | 12/2006 | DeVaul et al. |
| 2006/0287821 A1 | 12/2006 | Lin |
| 2006/0293571 A1 | 12/2006 | Bao et al. |
| 2007/0021134 A1 | 1/2007 | Liou |
| 2007/0064108 A1 | 3/2007 | Haler |
| 2007/0067079 A1 | 3/2007 | Kosugi |
| 2007/0091557 A1 | 4/2007 | Kim et al. |
| 2007/0102508 A1 | 5/2007 | McIntosh |
| 2007/0117083 A1 | 5/2007 | Winneg et al. |
| 2007/0132567 A1 | 6/2007 | Schofield et al. |
| 2007/0152811 A1 | 7/2007 | Anderson |
| 2007/0172053 A1 | 7/2007 | Poirier |
| 2007/0177023 A1 | 8/2007 | Beuhler et al. |
| 2007/0195939 A1 | 8/2007 | Sink et al. |
| 2007/0199076 A1 | 8/2007 | Rensin et al. |
| 2007/0213088 A1 | 9/2007 | Sink |
| 2007/0229350 A1 | 10/2007 | Scalisi et al. |
| 2007/0257781 A1 | 11/2007 | Denson |
| 2007/0257782 A1 | 11/2007 | Etcheson |
| 2007/0257804 A1 | 11/2007 | Gunderson et al. |
| 2007/0257815 A1 | 11/2007 | Gunderson et al. |
| 2007/0260361 A1 | 11/2007 | Etcheson |
| 2007/0268158 A1 | 11/2007 | Gunderson et al. |
| 2007/0271105 A1 | 11/2007 | Gunderson et al. |
| 2007/0274705 A1 | 11/2007 | Kashiwa |
| 2007/0277352 A1 | 12/2007 | Maron et al. |
| 2007/0285222 A1 | 12/2007 | Zadnikar |
| 2007/0287425 A1 | 12/2007 | Bates |
| 2007/0297320 A1 | 12/2007 | Brummette et al. |
| 2008/0001735 A1 | 1/2008 | Tran |
| 2008/0002031 A1 | 1/2008 | Cana et al. |
| 2008/0002599 A1 | 1/2008 | Yau et al. |
| 2008/0030580 A1 | 2/2008 | Kashhiwa et al. |
| 2008/0042825 A1 | 2/2008 | Denny et al. |
| 2008/0043736 A1 | 2/2008 | Stanley |
| 2008/0049830 A1 | 2/2008 | Richardson |
| 2008/0063252 A1 | 3/2008 | Dobbs et al. |
| 2008/0084473 A1 | 4/2008 | Romanowich |
| 2008/0100705 A1* | 5/2008 | Kister .............. G08B 13/19645 348/143 |
| 2008/0122603 A1 | 5/2008 | Plante et al. |
| 2008/0129518 A1 | 6/2008 | Carlton-Foss |
| 2008/0143481 A1 | 6/2008 | Abraham et al. |
| 2008/0144705 A1 | 6/2008 | Rackin et al. |
| 2008/0169929 A1 | 7/2008 | Albertson et al. |
| 2008/0170130 A1 | 7/2008 | Ollila et al. |
| 2008/0175565 A1 | 7/2008 | Takakura et al. |
| 2008/0211906 A1 | 9/2008 | Lovric |
| 2008/0222849 A1 | 9/2008 | Lavoie |
| 2008/0239064 A1 | 10/2008 | Iwasaki |
| 2008/0246656 A1 | 10/2008 | Ghazarian |
| 2008/0266118 A1 | 10/2008 | Pierson et al. |
| 2008/0307435 A1 | 12/2008 | Rehman |
| 2008/0316314 A1 | 12/2008 | Bedell et al. |

(56) References Cited

U.S. PATENT DOCUMENTS

| | | |
|---|---|---|
| 2009/0002491 A1 | 1/2009 | Haler |
| 2009/0002556 A1 | 1/2009 | Manapragada et al. |
| 2009/0027499 A1 | 1/2009 | Nicholl |
| 2009/0052685 A1 | 2/2009 | Cilia et al. |
| 2009/0070820 A1 | 3/2009 | Li |
| 2009/0085740 A1 | 4/2009 | Klein et al. |
| 2009/0109292 A1 | 4/2009 | Ennis |
| 2009/0122142 A1 | 5/2009 | Shapley |
| 2009/0135007 A1 | 5/2009 | Donovan et al. |
| 2009/0141129 A1 | 6/2009 | Dischinger |
| 2009/0169068 A1* | 7/2009 | Okamoto ............... 382/118 |
| 2009/0189981 A1 | 7/2009 | Siann et al. |
| 2009/0195686 A1 | 8/2009 | Shintani |
| 2009/0207252 A1 | 8/2009 | Raghunath |
| 2009/0213204 A1 | 8/2009 | Wong |
| 2009/0225189 A1 | 9/2009 | Morin |
| 2009/0243794 A1 | 10/2009 | Morrow |
| 2009/0251545 A1 | 10/2009 | Shekarri et al. |
| 2009/0252486 A1 | 10/2009 | Ross, Jr. et al. |
| 2009/0276708 A1 | 11/2009 | Smith et al. |
| 2009/0294538 A1 | 12/2009 | Wihlborg et al. |
| 2010/0045798 A1 | 2/2010 | Sugimoto et al. |
| 2010/0060734 A1 | 3/2010 | Chou |
| 2010/0060747 A1 | 3/2010 | Woodman |
| 2010/0097221 A1 | 4/2010 | Kreiner et al. |
| 2010/0106707 A1 | 4/2010 | Brown et al. |
| 2010/0118147 A1 | 5/2010 | Dorneich et al. |
| 2010/0122435 A1 | 5/2010 | Markham |
| 2010/0123779 A1 | 5/2010 | Snyder et al. |
| 2010/0177193 A1 | 7/2010 | Flores |
| 2010/0177891 A1 | 7/2010 | Keidar et al. |
| 2010/0188201 A1 | 7/2010 | Cook et al. |
| 2010/0191411 A1 | 7/2010 | Cook et al. |
| 2010/0194885 A1 | 8/2010 | Plaster |
| 2010/0217836 A1 | 8/2010 | Rofougaran |
| 2010/0238009 A1 | 9/2010 | Cook et al. |
| 2010/0238262 A1 | 9/2010 | Kurtz et al. |
| 2010/0242076 A1 | 9/2010 | Potesta et al. |
| 2010/0250021 A1 | 9/2010 | Cook et al. |
| 2010/0265331 A1 | 10/2010 | Tanaka |
| 2010/0274816 A1 | 10/2010 | Guzik |
| 2010/0028747 A1 | 11/2010 | Recesso et al. |
| 2011/0006151 A1 | 1/2011 | Beard |
| 2011/0018998 A1 | 1/2011 | Guzik |
| 2011/0050904 A1 | 3/2011 | Anderson |
| 2011/0069151 A1 | 3/2011 | Orimoto |
| 2011/0084820 A1 | 4/2011 | Walter et al. |
| 2011/0094003 A1 | 4/2011 | Spiewak et al. |
| 2011/0098924 A1 | 4/2011 | Baladeta et al. |
| 2011/0129151 A1 | 6/2011 | Saito et al. |
| 2011/0187895 A1 | 8/2011 | Cheng et al. |
| 2011/0261176 A1 | 10/2011 | Monaghan, Sr. et al. |
| 2011/0281547 A1 | 11/2011 | Cordero |
| 2011/0301971 A1 | 12/2011 | Roesch et al. |
| 2011/0314401 A1 | 12/2011 | Salisbury et al. |
| 2012/0038689 A1 | 2/2012 | Ishii |
| 2012/0056722 A1 | 3/2012 | Kawaguchi |
| 2012/0063736 A1 | 3/2012 | Simmons et al. |
| 2012/0120258 A1 | 5/2012 | Boutell et al. |
| 2012/0162436 A1 | 6/2012 | Cordell et al. |
| 2012/0188345 A1 | 7/2012 | Salow |
| 2012/0189286 A1 | 7/2012 | Takayama et al. |
| 2012/0195574 A1 | 8/2012 | Wallace |
| 2012/0230540 A1 | 9/2012 | Calman et al. |
| 2012/0268259 A1* | 10/2012 | Igel et al. ............... 340/426.11 |
| 2012/0276954 A1 | 11/2012 | Kowalsky |
| 2013/0021153 A1* | 1/2013 | Keays ............... 340/539.12 |
| 2013/0033610 A1 | 2/2013 | Osborn |
| 2013/0035602 A1* | 2/2013 | Gemer ............... A61B 5/0404 600/484 |
| 2013/0080836 A1 | 3/2013 | Stergiou et al. |
| 2013/0096731 A1 | 4/2013 | Tamari et al. |
| 2013/0125000 A1 | 5/2013 | Flischhauser et al. |
| 2013/0148295 A1 | 6/2013 | Minn et al. |
| 2013/0222640 A1 | 8/2013 | Baek et al. |
| 2013/0225309 A1 | 8/2013 | Bentley et al. |
| 2013/0285232 A1 | 10/2013 | Sheth |
| 2013/0290018 A1 | 10/2013 | Anderson et al. |
| 2013/0300563 A1 | 11/2013 | Glaze |
| 2013/0343572 A1 | 12/2013 | Lee |
| 2014/0037262 A1 | 2/2014 | Sako |
| 2014/0049636 A1 | 2/2014 | O'Donnell et al. |
| 2014/0092299 A1 | 4/2014 | Phillips et al. |
| 2014/0094992 A1 | 4/2014 | Lambert et al. |
| 2014/0098453 A1 | 4/2014 | Brundula et al. |
| 2014/0140575 A1 | 5/2014 | Wolf |
| 2014/0170602 A1 | 6/2014 | Reed |
| 2014/0192194 A1 | 7/2014 | Bedell et al. |
| 2014/0195105 A1 | 7/2014 | Lambert et al. |
| 2014/0195272 A1 | 7/2014 | Sadiq et al. |
| 2014/0210625 A1 | 7/2014 | Nemat-Nasser |
| 2014/0218544 A1 | 8/2014 | Senot et al. |
| 2014/0227671 A1* | 8/2014 | Olmstead et al. ............ 434/308 |
| 2014/0311215 A1* | 10/2014 | Keays et al. ............... 73/23.3 |
| 2014/0341532 A1 | 11/2014 | Marathe et al. |
| 2014/0355951 A1 | 12/2014 | Tabak |
| 2015/0050003 A1 | 2/2015 | Ross et al. |
| 2015/0051502 A1 | 2/2015 | Ross |
| 2015/0063776 A1 | 3/2015 | Ross et al. |
| 2015/0078727 A1 | 3/2015 | Ross et al. |
| 2015/0088335 A1 | 3/2015 | Lambert et al. |
| 2015/0103246 A1 | 4/2015 | Phillips et al. |
| 2015/0229630 A1 | 8/2015 | Smith |
| 2015/0317368 A1 | 11/2015 | Rhoads et al. |
| 2015/0332424 A1 | 11/2015 | Kane et al. |
| 2015/0358549 A1 | 12/2015 | Cho et al. |
| 2016/0042767 A1* | 2/2016 | Araya ............... G11B 19/02 386/201 |
| 2016/0050345 A1 | 2/2016 | Longbotham |
| 2016/0104508 A1* | 4/2016 | Chee ............... H04N 21/2743 725/93 |
| 2016/0127695 A1 | 5/2016 | Zhang et al. |
| 2016/0165192 A1 | 6/2016 | Saatchi et al. |
| 2016/0364621 A1 | 12/2016 | Hill et al. |
| 2017/0070659 A1 | 3/2017 | Kievsky et al. |
| 2017/0195635 A1 | 7/2017 | Yokomitsu et al. |
| 2017/0200476 A1 | 7/2017 | Chen et al. |
| 2017/0230605 A1 | 8/2017 | Han et al. |
| 2017/0237950 A1 | 8/2017 | Araya et al. |
| 2017/0244884 A1 | 8/2017 | Burtey et al. |
| 2017/0277700 A1 | 9/2017 | Davis et al. |
| 2017/0287523 A1 | 10/2017 | Hodulik et al. |
| 2018/0023910 A1 | 1/2018 | Kramer |
| 2018/0050800 A1 | 2/2018 | Boykin et al. |

FOREIGN PATENT DOCUMENTS

| | | |
|---|---|---|
| GB | 2273624 | 6/1994 |
| GB | 2320389 | 6/1998 |
| GB | 2343252 | 5/2000 |
| GB | 2351055 | 12/2000 |
| GB | 2417151 | 2/2006 |
| GB | 2425427 | 10/2006 |
| GB | 2455885 | 7/2009 |
| GB | 2485804 A | 5/2012 |
| IE | 20090923 A1 | 9/2010 |
| JP | 294188 | 9/1993 |
| JP | 153298 | 6/1996 |
| JP | 198858 | 7/1997 |
| JP | 10076880 A | 3/1998 |
| JP | 210395 | 7/1998 |
| JP | 2000137263 A | 5/2000 |
| JP | 2005119631 A | 5/2005 |
| KR | 1050897 | 7/2011 |
| RU | 2383915 C2 | 3/2010 |
| WO | WO9005076 | 5/1990 |
| WO | WO9738526 | 10/1997 |
| WO | WO9831146 | 7/1998 |
| WO | 9948308 | 9/1999 |
| WO | WO0039556 | 7/2000 |
| WO | WO0051360 | 8/2000 |
| WO | 0123214 A1 | 4/2001 |
| WO | 0249881 | 5/2002 |
| WO | WO0249881 | 6/2002 |

(56) References Cited

FOREIGN PATENT DOCUMENTS

| WO | WO02095757 | 11/2002 |
|---|---|---|
| WO | WO03049446 | 6/2003 |
| WO | 2004036926 A2 | 4/2004 |
| WO | 2009013526 A1 | 1/2009 |
| WO | 211001180 A1 | 1/2011 |
| WO | 2012037139 A2 | 3/2012 |
| WO | 2012120083 A1 | 9/2012 |
| WO | 2014000161 A1 | 1/2014 |
| WO | 2014052898 A1 | 4/2014 |

OTHER PUBLICATIONS

Notification of Transmittal of the International Search Report and the Written Opinion of the International Searching Authority, or the Declaration dated Jan. 30, 2014; International Application No. PCT/US2013/062415; International Filing Date: Sep. 27, 2013; Applicant: Digital Ally, Inc.

Taser Axon Body on Officer Video/Police Body Camera, http://www.taser.com/products/on-officer-video/axon-body-on-officer-video, Sep. 23, 2013, Date Posted: Unknown, pp. 1-8.

GoPro Official Website: The World's Most Versatile Camera, http://gopro.com/products/?gclid=CKqHy9jT4rkCFWZk7AodyiAAaQ, Sep. 23, 2013, Date Posted: Unknown, pp. 4-9.

Vievu Products, http://www.vievu.com/vievu-products/vievu-squared/, Sep. 25, 2013, Date Posted: Unknown, pp. 1-2.

Digital Ally First Vu Mountable Digital Camera Video Recorder, http://www.opticsplanet.com/digital-ally-first-vu-mountable-digital-camera-video-recorder.html?gclid=CIKohcX05rkCFSIo7AodU0IA0g&ef_id=UjCGEAAAAWGEjrQF:20130925155534:s, Sep. 25, 2013, Date Posted: Unknown, pp. 1-4.

Taser Axon Flex On-Officer Video/Police Video Camera, http://www.taser.com/products/on-officer-video/taser-axon, Sep. 26, 2013, Date Posted: Unknown, pp. 1-8.

Zepcam Wearable Video Technology, http://www.zepcam.com/product.aspx, Sep. 26, 2013, Date Posted: Unknown, pp. 1-2.

Witness Cam headset, http://www.secgru.com/DVR-Witness-Cam-Headset-Video-Recorder-SG-DVR-1-COP.html, Sep. 26, 2013, Date Posted: Unknown, pp. 1-2.

SUV Cam, http://www.elmo.co.jp/suv-cam/en/product/index.html, Sep. 26, 2013, Date Posted: Unknown, p. 1.

Asian Wolf High Quality Angel Eye Body Video Spy Camera Recorder System, http://www.asianwolf.com/covert-bodycam-hq-angeleye.html, Sep. 26, 2013, Date Posted: Unknown, pp. 1-3.

Panasonic Handheld Avccam HD Recorder/Player, http://www.panasonic.com/business/provideo/ag-hmr10.asp, Sep. 26, 2013, Date Posted: Unknown, pp. 1-2.

POV.HD System Digital Video Camera, http://www.vio-pov.com/index.php, Sep. 26, 2013, Date Posted: Unknown, pp. 1-3.

Ecplaza HY-001HD law enforcement DVR, http://fireeye.en.ecplaza.net/law-enforcement-dvr--238185-1619696.html, Sep. 26, 2013, Date Posted: Unknown, pp. 1-3.

Edesix VideoBadge, http://www.edesix.com/edesix-products, Sep. 26, 2013, Date Posted: Unknown, pp. 1-3.

Tide Leader police body worn camera, http://tideleader.en.gongchang.com/product/14899076, Sep. 26, 2013, Date Posted: Unknown, pp. 1-3.

Stalker VUE Law Enforcement Grade Body Worn Video Camera/Recorder, http://www.stalkerradar.com/law_vue.shtml, Sep. 26, 2013, Date Posted: Unknown, pp. 1-2.

Vidmic Officer Worn Video & Radio Accessories, http://www.vidmic.com/, Sep. 26, 2013, Date Posted: Unknown, p. 1.

WatchGuard CopVu Wearable Video Camera System, http://watchguardvideo.com/copvu/overview, Sep. 26, 2013, Date Posted: Unknown, pp. 1-2.

Kustom Signals VieVu, http://www.kustomsignals.com/index.php/mvideo/vievu, Sep. 26, 2013, Date Posted: Unknown, pp. 1-4.

WolfCom 3rd Eye, X1 A/V Recorder for Police and Military, http://wolfcomusa.com/Products/Products.html, Sep. 26, 2013, Date Posted: Unknown, pp. 1-3.

Reveal Media RS3-SX high definition video recorder, http://www.revealmedia.com/buy-t166/cameras/rs3-sx.aspx, Sep. 26, 2013, Date Posted: Unknown, pp. 1-2.

Spy Chest Mini Spy Camera / Self Contained Mini camcorder / Audio & Video Recorder, http://www.spytechs.com/spy_cameras/mini-spy-camera.htm, Sep. 26, 2013, Date Posted: Unknown, pp. 1-3.

LEA-AID SCORPION Micro Recorder Patrol kit,http://www.leacorp.com/products/SCORPION-Micro-Recorder-Patrol-kit.html, Sep. 26, 2013, Date Posted: Unknown, pp. 1-2.

Veho MUVI portable wireless speaker with dock, http://veho-uk.fastnet.co.uk/main/shop.aspx?category=camcorder, Sep. 26, 2013, Date Posted: Unknown, p. 1.

Veho MUVI HD, http://veho-uk.fastnet.co.uk/main/shop.aspx?category=CAMMUVIHD, Sep. 26, 2013, Date Posted: Unknown, pp. 1-5.

SIV Security in Vehicle Driving Partner, http://www.siv.co.kr/, Sep. 26, 2013, Date Posted: Unknown, p. 1.

Midland XTC HD Video Camera, http://midlandradio.com/Company/xtc100-signup, Sep. 26, 2013, Date Posted: Unknown, pp. 1-3.

Drift X170, http://driftinnovation.com/support/firmware-update/x170/, Sep. 26, 2013, Date Posted: Unknown, p. 1.

UCorder Pockito Wearabel Mini Pcket Camcorder, http://www.ucorder.com/, Sep. 26, 2013, Date Posted: Unknown, p. 1.

Isaw Advance Hull HD EXtreme, www.isawcam.co.kr, Sep. 26, 2013, Date Posted: Unknown, p. 1.

Scorpion Micro DV Video Audio Recorder, http://www.leacorp.com/scorpion-micro-dv-video-audio-recorder/, Sep. 26, 2013, Date Posted: Unknown, pp. 1-3.

Taser Cam Law Enforcement Audio/Video Recorder (gun mounted), http://www.taser.com/products/on-officer-video/taser-cam, Sep. 26, 2013, Date Posted: Unknown, pp. 1-3.

Looxcie Wearable & mountable streaming video cams, http://www.looxcie.com/overview?gclid=CPbDyv6piq8CFWeFQAodlhXC-w, Sep. 26, 2013, Date Posted: Unknown, pp. 1-4.

Point of View Cameras Military & Police, http://pointofviewcameras.com/military-police, Sep. 26, 2013, Date Posted: Unknown, pp. 1-2.

Dyna Spy Inc. hidden cameras, https://www.dynaspy.com/hidden-cameras/spy-cameras/body-worn-wearable-spy-cameras, Sep. 26, 2013, Date Posted: Unknown, pp. 1-3.

Amazon.com wearable camcorders, http://www.amazon.com/s/ref=nb_sb_ss_i_0_4?url=search-alias%3Dphoto&field-keywords=wearable+camcorder&x=0&y=0&sprefix=wear, Sep. 26, 2013, Date Posted: Unknown, pp. 1-4.

Oregon Scientific ATC Chameleon Dual Lens HD Action Camera, http://www.oregonscientificstore.com/Oregon-Scientific-ATC-Chameleon-Dual-Lens-HD-Action-Camera.data, Date Posted: Unknown; Date Printed: Oct. 13, 2014, pp. 1-4.

Freudenrich, Craig, Ph.D.; "How Breathalyzers Work—Why Test?." HowStuffWorks. Printed Date: Oct. 16, 2014; Posted Date: Unknown; <http://electronics.howstuffworks.com/gadgets/automotive/breathalyzer1.htm>.

"Breathalyzer." Wikipedia. Printed Date: Oct. 16, 2014; Date Page Last Modified: Sep. 14, 2014; <http://en.wikipedia.org/wiki/Breathalyzer>.

Renstrom, Joell; "Tiny 3D Projectors Allow You to Transmit Holograms From a Cell Phone." Giant Freakin Robot. Printed Date: Oct. 16, 2014; Posted Date: Jun. 13, 2014; <http://www.giantfreakinrobot.com/sci/coming-3d-projectors-transmit-holograms-cell-phone.html>.

Kopin Corporation; Home Page; Printed Date: Oct. 16, 2014; Posted Date: Unknown; <http://www.kopin.com>.

Wasson, Brian; "Digital Eyewear for Law Enforcement." Printed Date: Oct. 16, 2014; Posted Date: Dec. 9, 2013; <http://www.wassom.com/digital-eyewear-for-law-enforcement.html>.

"Stalker Press Room—Using In-Car Video, the Internet, and the Cloud to keep police officers safe is the subject of CopTrax live, free webinar." Stalker. Printed Date: Oct. 16, 2014; Posted Date: Jul. 31, 2014.

Brick House Security Body Worn Cameras / Hidden Cameras / Covert Spy Cameras, http://www.brickhousesecurity.com, Date Printed: Sep. 26, 2013, Date Posted: Unknown, pp. 1-2.

(56) References Cited

OTHER PUBLICATIONS

Notification of Transmittal of the International Search Report and the Written Opinion of the International Searching Authority, or the Declaration dated Jan. 21, 2016; International Application No. PCT/US2015/056062; International Filing Date: Oct. 16, 2015; Applicant: Digital Ally, Inc.
File History of Request for Ex Parte Reexamination of U.S. Pat. No. 8,781,292 as submitted on Apr. 16, 2015; Control No. 901013,489.
Controller Area Network (CAN) Overview, National Instruments White Paper (Aug. 1, 2014).
Brown, TP-LINK TL-WDR3500 Wireless N600 Router Review, Mar. 6, 2013.
Guide to Bluetooth Security: Recommendations of the National Institute of Standards and Technology, National Institute of Standards and Technology, U.S. Dep't of Commerce, NIST Special Publication 800-121, Revision 1 (Jun. 2012).
Notification Concerning Transmittal of Copy of International Preliminary Report on Patentability (Chapter I of the Patent Cooperation Treaty) dated Apr. 9, 2015; International Application No. PCT/US2013/062415; International Filing Date: Sep. 27, 2013; Applicant: Digital Ally, Inc.
Request for Comment 1323 of the Internet Engineering Task Force, TCP Extensions for High Performance, Date: May 1992.
W. Fincham, Data Recorders for Accident Investigation, Monitoring of Driver and Vehicle Performance (Digest No. 1997/122), Publication Date: Apr. 10, 1997, pp. 6/1-6/3.
S.R. Lewis, Future System Specifications for Traffic Enforcement Equipment, S.R. 1 Source: IEE Colloquium (Digest), N 252, Publication Date: Nov. 18, 1996, pp. 8/1-8/2.
Samuel W. Daskam, Law Enforcement Armed Robbery Alarm System Utilizing Recorded Voice Addresses via Police Radio Channels, Source: Univ. of Ky, Off of Res and Eng., Sery (UKY BU107), pp. 18-22, 1975.
New Rearview-Mirror-Based Camera Display Takes the Guesswork Out of Backing Up Retrieved from the Internet: <URL: httb://news.thomasnet.com/fullstory/497750>, Press Release, Oct. 30, 2006.
Lilliput RV 18-50NP 5" Rear View Mirror TFT LCD Screen with Camera, Retrieved from the Internet: <URL: http://www.case-mod.com/lilliput-rv1850np-rear-view-mirror-tft-lcd-screen-with-camera-p-1271.html>, Mar. 4, 2005.
Car Rear View Camera—Multimedia Rear View Mirror—4' LCD color monitor, Retrieved from the Internet: <URL: http://web.archive.org/web/20050209014751/http://laipac.com/multimedia-rear-mirrorhtm>, Feb. 9, 2005.
Frankel, Harry; Riter, Stephen, Bernat, Andrew, Automated Imaging System for Border Control, Source: University of Kentucky, Office of Engineering Services, (Bulletin) UKY BU, pp. 169-173, Aug. 1986.
Supplementary European Search Report dated Sep. 28, 2010 in European Patent Application No. 06803645.8; Applicant: Digital Ally, Inc.
Korean Utility Model Reg. No. 20-0236817, published Oct. 8, 2001.
SIIF Award for Multi Black Box, published Dec. 10, 2004.
Automation Systems Article, Know-How Bank Co. Ltd. Takes Leap Forward as a Company Specializing in R&D and Technology Consulting, published Jan. 2005.
Electronic Times Article, published Feb. 24, 2005.
Motor Magazine Article, Recreating the Scene of an Accident, published 2005.
Hankyung Auto News Article, Know-How Bank's Black Box for Cars "Multi-Black Box," Copyright 2005.
http://www.k-h-b.com/board/board.php?board=products01&comand=body&no=1, Current State of Technology Held by the Company, Copyright 2005.
File History of U.S. Appl. No. 13/967,151, filed Aug. 14, 2013, entitled Computer Program, Method, and System for Managing Multiple Data Recording Devices; Applicant: Digital Ally, Inc.
File History of U.S. Appl. No. 14/040,233, filed Sep. 27, 2013, entitled Computer Program, Method, and System for Managing Multiple Data Recording Devices; Applicant: Digital Ally, Inc.
File History of U.S. Appl. No. 14/517,368, filed Oct. 17, 2014, entitled Forensic Video Recording With Presence Detection; Applicant: Digital Ally, Inc.
ATC Chameleon. Techdad Review [Online] Jun. 19, 2013 [Retrieved on Dec. 30, 2015]. Retrieved from Internet. <URL:http://www.techdadreview.com/2013/06/19atc-chameleon/>.
*Digital Ally* vs. *Taser International, Inc.*, Case No. 2:16-cv-232 (CJWTJ); US D. Kan, Defendant Taser International Inc.'s Preliminary Invalidity Contentions, Jul. 5, 2016.
ICOP Extreme Wireless Mic, Operation Supplement, Copyright 2008.
Bertomen, Lindsey J., PoliceOne.com News; "Product Review: ICOP Model 20/20-W," May 19, 2009.
Translation of Korean Patent No. 10-1050897, published Jul. 20, 2011.
Notification of Transmittal of the International Search Report and the Written Opinion of the International Search Authority, or the Declaration dated Jan. 14, 2016, International Application No. PCT/US2015/056039; International Filing date Oct. 16, 2015, Applicant: Digital Ally, Inc.
City of Pomona Request for Proposals for Mobile Video Recording System for Police Vehicles, dated prior to Apr. 4, 2013.
U.S. Appl. No. 15/011,132 Office Action dated Apr. 18, 2016, 19 pages.
State of Utah Invitation to Bid State Cooperative Contract; Vendor: ICOP Digital, Inc., Contract No. MA503, Jul. 1, 2008.
Taser International; Taser X26 Specification Sheet, 2003.
Dees, Tim; Taser Axon Flex: The next generation of body camera; <http://www.policeone.com/police-products/body-cameras/articles/527231- 0-TASER-Axon-Flex-The-next-generation-of-body-camera/>, Date Posted: Mar. 12, 2012; Date Printed: Oct. 27, 2015.
European Patent Application 15850436.6 Search Report dated May 4, 2018.
Final Written Decision for Inter Partes Review No. 2017-00375, *Axon Enterprise Inc.* v. *Digital Ally, Inc.*, dated Jun. 1, 2018.
PCT Patent Application PCT/US17/16383 International Search Report and Written Opinion dated May 4, 2017.
*Digital Ally, Inc.* vs. *Taser International, Inc.*, Case No. 2:16-cv-020232 (CJM/TJ); US D. Kan, Complaint for Patent Infringement, Jan. 14, 2016.
*Digital Ally, Inc.* vs. *Enforcement video LLC d/b/a Watchguard Video.*, Case No. 2:16-cv-02349 (CJMITJ); US D. Kan, Complaint for Patent Infringement, May 27, 2016.
International Association of Chiefs of Police Digital Video System Minimum Specifications; Nov. 21, 2008.
Petition for Inter Partes Review No. 2017-00375, *Taser International, Inc.* v. *Digital Ally, Inc.*, filed Dec. 1, 2013.
Petition for Inter Partes Review No. 2017-00376, *Taser International, Inc.* v. *Digital Ally, Inc.*, filed Dec. 1, 2013.
Petition for Inter Partes Review No. 2017-00515, *Taser International, Inc.* v. *Digital Ally Inc.*, filed Jan. 11, 2017.
Petition for Inter Partes Review No. 2017-00775, *Taser International, Inc.* v. *Digital Ally Inc.*, filed Jan. 25, 2017.
PCT Patent Application PCT/US16/34345 International Search Report and Written Opinion dated Dec. 29, 2016.
State of Utah Invitation to Bid State Cooperative Contract; Vendor: Kustom Signals Inc., Contract No. MA1991, Apr. 25, 2008.
Invalidity Chart for International Publication No. WO2014/000161 Oct. 31, 2017.
Petition for Post Grant Review No. PGR2018-00052, *Axon Enterprise, Inc.* v. *Digital Ally, Inc.*, filed Mar. 19, 2018.
MPEG-4 Coding of Moving Pictures and Audio ISO/IEC JTC1/SC29/WG11 N4668 dated Mar. 2002.
Decision Denying Institution of Post Grant Review for Post Grant Review No. PGR2018-00052, *Axon Enterprise, Inc.* v. *Digital Ally, Inc.*, dated Oct. 1, 2018.

\* cited by examiner

BREATH ANALYZER, SYSTEM, AND COMPUTER PROGRAM FOR AUTHENTICATING, PRESERVING, AND PRESENTING BREATH ANALYSIS DATA

RELATED APPLICATIONS

This non-provisional patent application is a continuation-in-part application and claims priority benefit, with regard to all common subject matter, of commonly assigned U.S. patent application Ser. No. 13/967,151, filed Aug. 14, 2013, and entitled "COMPUTER PROGRAM, METHOD, AND SYSTEM FOR MANAGING MULTIPLE DATA RECORDING DEVICES" ("the '151 Application"). The '151 Application is hereby incorporated by reference in its entirety into the present application.

Embodiments and/or features of the invention described in the present document may be used with the subject matter disclosed in commonly assigned U.S. Pat. No. 8,781,292, filed Sep. 27, 2013, issued Jul. 15, 2014, and entitled "COMPUTER PROGRAM, METHOD, AND SYSTEM FOR MANAGING MULTIPLE DATA RECORDING DEVICES" ("the '292 Patent"), which is a continuation application of the '151 Application. The '292 Patent is hereby incorporated by reference in its entirety into the present application.

Embodiments and/or features of the invention described in the present document may be used with the subject matter disclosed in commonly assigned U.S. patent application Ser. No. 14/040,329, filed Sep. 27, 2013, and entitled "PORTABLE VIDEO AND IMAGING SYSTEM" ("the '329 Application"); and commonly assigned U.S. patent application Ser. No. 14/040,006, filed Sep. 27, 2013, and entitled "MOBILE VIDEO AND IMAGING SYSTEM" ("the '006 Application"). The '329 Application and the '006 Application are hereby incorporated by reference in their entirety into the present application.

Further, embodiments and/or features of the invention described in the present document may be used with the subject matter disclosed in commonly assigned and concurrently filed U.S. patent application Ser. No. 14/517,226 filed Oct. 17, 2014, and entitled "DUAL LENS CAMERA UNIT," and with concurrently filed and commonly assigned U.S. patent application Ser. No. 14/517,368 filed Oct. 17, 2014, and entitled "FORENSIC VIDEO RECORDING WITH PRESENCE DETECTION." Each of the concurrently filed patent applications is also a continuation-in-part of the '151 Application. The concurrently filed patent applications are hereby incorporated by reference in their entirety into the present application.

BACKGROUND

1. Field

Embodiments of the invention relate to breath analyzing devices. More specifically, embodiments of the invention relate to the authentication of a breath analysis, the preservation of the breath analysis result, and the presentation of the breath analysis result.

2. Related Art

Breath analysis devices, commonly known as Breathalyzers® and Intoxilyzers®, estimate the amount of a chemical substance, such as alcohol, in a breath sample. Breath analysis devices do not directly measure blood alcohol content or concentration in the blood but instead estimate the blood alcohol content or concentration by measuring the amount of alcohol found in a breath sample from a donor. Breath analysis results are used as evidence in criminal and civil cases. Authenticating, preserving, and presenting the results is therefore important for purposes of establishing criminal activity.

Breath analysis devices of the prior art present numerous drawbacks. First, there is no authentication of the donor (i.e., the individual providing the breath sample), how the breath analysis was performed, and which administrator (e.g., a law enforcement officer) performed the breath analysis. The only verification of these can be based upon human testimony and independent videos or photographs taken by the administrator. Second, breath analysis devices present the result only on a display of the device. This requires the administrator to clearly read, recall, and record the displayed result. For example, the administrator may write the result in his notes or take a photograph of the device showing the result. Both of these methods require additional work by the administrator and record the result in disparate locations that could become lost or destroyed. Third, breath analysis devices of the prior art do not present the results in a manner easily displayed in a courtroom. Typically, the administrator testifies to the result of the breath analysis or presents photographs of the device displaying the breath analysis result. Both of these are prone to human error and can raise doubt in the judge or jury.

SUMMARY

Embodiments of the invention solve the above-mentioned problems by providing a breath analyzer, system, and computer program for authenticating, preserving, and presenting the results of a breath analysis. First, embodiments of the invention authenticate that the breath analysis was performed correctly by integrating video from at least one ancillary video camera and/or an integral video camera on the breath analyzer with the breath analysis result. Embodiments may also authenticate which administrator performed the breath analysis by a proximity tag system in the breath analyzer and/or a recording device manager. Second, embodiments of the invention preserve the results of the breath analysis by communicating the results to the recording device manager and/or the ancillary video camera, and storing the breath analysis results in metadata of the recorded video. Third, embodiments present the breath analysis result of the breath analyzer by superimposing the result onto the video recorded by the ancillary video cameras and/or the integral video camera on the breath analyzer.

A first embodiment of the invention is directed to a system for authenticating, preserving, and presenting breath analysis data. The system comprises the breath analyzer, the recording device manager, the at least one ancillary video camera, and an auxiliary computing device (which may be housed with any of the aforementioned components or be housed in a separate housing).

A second embodiment of the invention is directed to the breath analyzer, which is adapted to authenticate the breath analysis procedure and the administrator and to preserve breath analysis data by communicating the result with a recording device manager. The breath analyzer is a handheld device used by the administrator to perform the breath analysis on the donor. The breath analyzer comprises a breath receptor, an analyzing element, at least one processing element, a communications element, a memory element, and a housing.

A third embodiment of the invention is directed to a non-transitory computer readable storage medium associated with or otherwise stored within the breath analyzer that has a computer program stored thereon that instructs at least one processing element of the breath analyzer to perform the steps of a computerized method of authenticating the breath analysis and preserving the breath analysis result. The computerized method may also be directed to presenting the breath analysis result.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
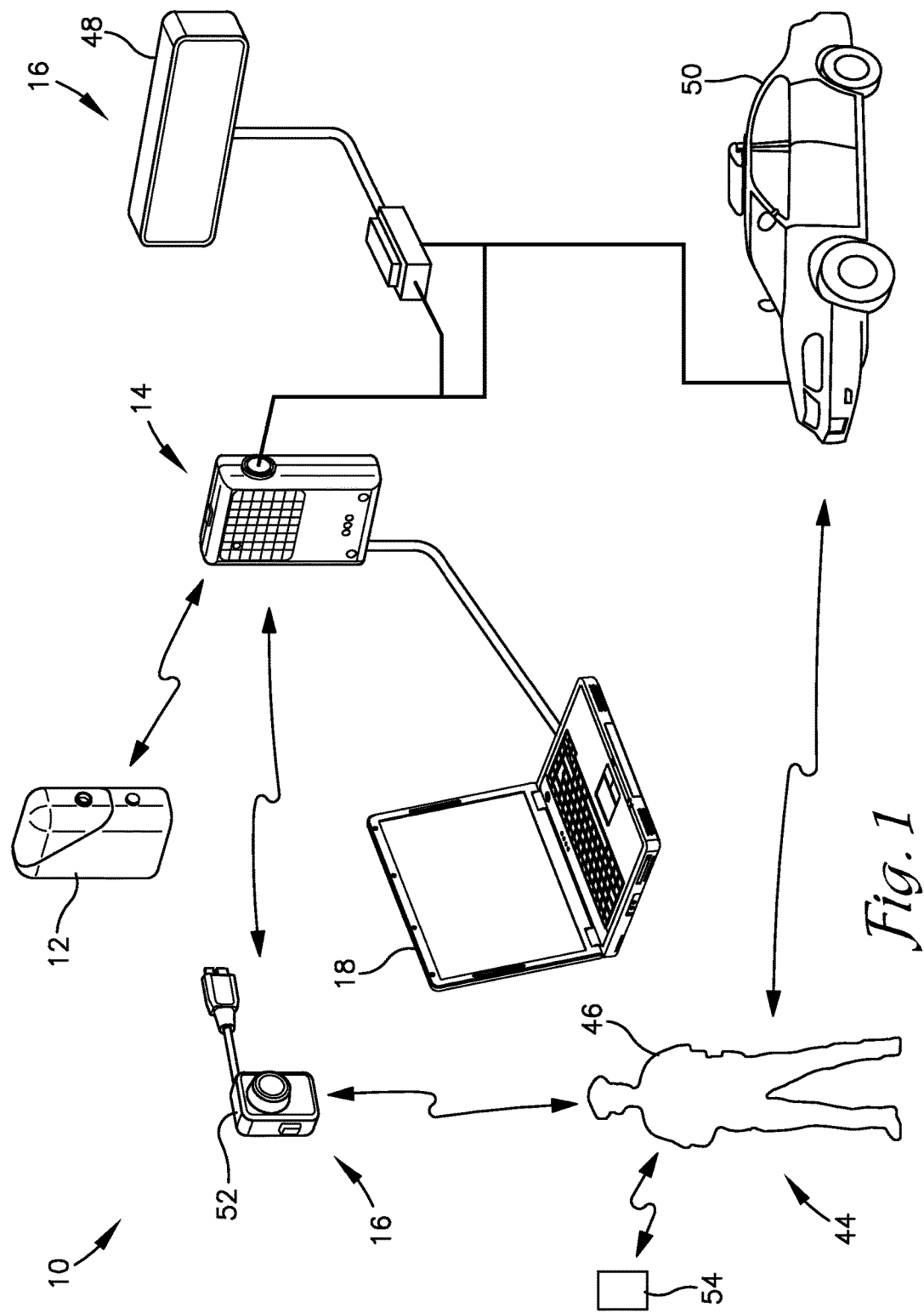
FIG. 1 is a system diagram illustrating the interactions of the various components of the system.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Turning to FIG. 1, embodiments of the invention are directed to a system 10 for authenticating, preserving, and presenting breath analysis data. The system 10 comprises a breath analyzer 12, a recording device manager 14, at least one ancillary video camera 16, and an auxiliary computing device 18, which may include display, processing, and storage capabilities. In some embodiments auxiliary computing device takes the form of a laptop computer in law enforcement vehicle 50. In other embodiments it takes the form of a mobile device carried by law enforcement officer 46. Other form factors for auxiliary computing device 18 are also contemplated. The system 10 authenticates that the breath analysis was performed correctly by recording the breath analysis with the at least one ancillary video camera 16, and in some embodiments an integral video camera 20 in the breath analyzer 12. A donor 22 provides a breath sample to the breath analyzer 12. The breath analyzer 12 then sends an "analysis in progress" status 24 while it analyzes the breath sample to determine a breath analysis result 26. The system 10 then preserves the breath analysis result by transmitting the breath analysis result to the recording device manager 14 for preservation at auxiliary computing device 18 and saving the breath analysis result as metadata. The system 10 also presents the breath analysis result by superimposing data onto the video recording from the ancillary video camera 16 and/or the integral video camera 20. In some embodiments, the breath analysis is also displayed in real time on a display of one or more computing devices such as auxiliary computing device 18. In some such embodiments, the breath analysis result is superimposed on video displayed from one or more video cameras such as ancillary video camera 16. In other embodiments, it is displayed on a dedicated portion of a display screen. In still other embodiments it is displayed on a dedicated display device such as a readout in law enforcement vehicle 50 or a heads-up display (HUD) worn by law enforcement officer 46.

Other embodiments of the system 10 may comprise the breath analyzer 12, the recording device manager 14, and the auxiliary computing device 18. The breath analyzer 12 transmits the breath analysis result to the recording device manager 14, which stores the breath analysis result at auxiliary computing device 18 without any video or superimposing. Still other embodiments of the system 10 may comprise the breath analyzer 12 and the at least one ancillary video camera 16, in which the breath analyzer 12 communicates directly with the ancillary video camera 16.

The system 10 of embodiments of the invention may comprise computing devices to facilitate the functions and features described herein. The computing devices may comprise any number and combination of processors, controllers, integrated circuits, programmable logic devices, or other data and signal processing devices for carrying out the functions described herein, and may additionally comprise one or more memory storage devices, transmitters, receivers, displays, and/or communication busses for communicating with the various devices of the system 10.

Embodiments of the invention are also directed to the breath analyzer 12. The breath analyzer 12 is a relatively small, hand held device for receiving and analyzing a breath sample. The breath analyzer 12 comprises a breath receptor 28, an analyzing element 30, a processing element 32, a communications element 34, a memory element 36, and a housing 38. The breath analyzer 12 may further comprise a battery, at least one user input 40, at least one status indicator, a display 42, a data cable, and/or a power cable.

Embodiments of the invention are also directed to a method of authenticating, preserving, and presenting breath analysis data. An administrator 44 administers the breath analysis. The administrator 44 may authenticate their identity with the breath analyzer 12 and/or recording device manager 14. The administrator 44 may also authenticate the breath analysis is performed correctly by directing at least one ancillary video camera 16 toward the location in which the breath analysis will be performed. The administrator 44 directs the donor 22 to blow into the breath receptor 28 for a certain period of time. The particles expelled by the donor 22 are the breath sample. The analyzing element 30 within the breath analyzer 12 detects and measures the level of at least one chemical compound, such as alcohol or ethanol, in the breath sample. The breath analyzer 12 then preserves the breath analysis result data by transmitting information indicative of the breath analysis result to the recording device manager 14. The breath analyzer 12 may also display the result for the administrator 44 and donor 22 on one or more displays, as described above. The recording device manager 14 associates the breath analysis data with the video being captured by the ancillary video cameras 16. The breath analysis result may also be presented by superimposing the breath analysis result onto the video being recorded.

It should be appreciated that while the current disclosure is largely directed to the detection of alcohol impairment by law enforcement, other embodiments of the invention may be directed to other fields. Embodiments of the invention may be directed to the breath analysis and detection of other substances, such as tobacco, marijuana, cocaine, amphetamines, opioids, MDMA, and other illicit substances. Embodiments of the invention may additionally or in the alternative be directed to other purposes of breath analysis, such as vehicle interlock devices, parole/probation assessments, new/potential/periodic employee screenings, impairment screenings for workers' compensation injuries, testing by alcohol servers, and self-testing.

Breath analysis is often used by a law enforcement officer 46 to determine the level of intoxication of drivers on roadways. In this scenario, the donor 22 is the driver suspected of operating a vehicle while intoxicated, and the administrator 44 is the law enforcement officer 46 or officers administering the breath analysis. The result of the breath analysis may give the law enforcement office probable cause to arrest the driver. The result of the breath analysis may also be presented in court as evidence of the driver's intoxication. However, in some states, the breath analysis results of "preliminary breath testers" ("PBTs", i.e. the handheld devices carried by law enforcement officers 46) are inadmissible at trial, because PBTs are not calibrated and tested as often as "evidentiary breath testers" which are usually located at a central law enforcement facility. While the breath analysis may be less accurate than a direct blood or urine tests, breath analysis provides the benefits of being non-invasive, simple to execute, and able to provide quick results.

The donor 22 is the person whose breath is to be analyzed to estimate the content of a certain substance in their blood. The donor 22 may be a driver suspected of driving while intoxicated, a potential employee, an employee that has recently been injured on the job, a person on parole or probation, a government benefits recipient, etc. The donor 22 may refuse to provide the breath sample, but this may have other legal and employment consequences.

A portion of the alcohol, or other substances, that the donor 22 has consumed are expelled with each breath, because the alcohol was absorbed into the blood stream via the donor's mouth, throat, stomach, intestine, etc. As the alcohol travels through the blood stream, it reaches the donor's lungs. Because alcohol is volatile (i.e., it will evaporate from a liquid solution), a portion of the alcohol evaporates into the lungs and is expelled along with the air during exhalation. The concentration of alcohol in the breath is related by a known formula to the concentration of alcohol in the blood. The breath analyzer 12 therefore tests the breath sample of the donor 22 and calculates an estimation of the donor's blood alcohol concentration ("BAC", also known as blood alcohol content). The BAC is typically measured in the units of grams/100 mL. The current legal limit throughout the United States is 0.08 grams/100 mL.

The administrator 44 oversees the breath analysis. The administrator 44 may closely observe the donor 22 for a period of time before the breath analysis. This is to ensure that the donor 22 does not have any alcohol in his mouth or throat, which can provide inaccurate test results. The administrator 44 may also direct the at least one ancillary cameras to the area in which the breath analysis will take place, to provide a plurality of viewing angles of the breath analysis. For example, there may be a vehicle-mounted 48 ancillary video camera 16 in a law enforcement vehicle 50, a person-mounted 52 ancillary camera on the administrator 44, and another person-mounted 52 ancillary video camera 16 on an assistant administrator (e.g., another law enforcement officer). The administrator 44 may also provide instructions to the donor 22, such as how to blow into the breath analyzer 12 and for what amount of time. The administrator 44 may also manipulate the breath analyzer 12, such as by turning the breath analyzer 12 on. During the breath analysis, the administrator 44 observes the donor 22 to ensure proper procedures are followed. If not, the administrator 44 may correct the donor 22 and re-initiate the breath analysis.

Figure 5:
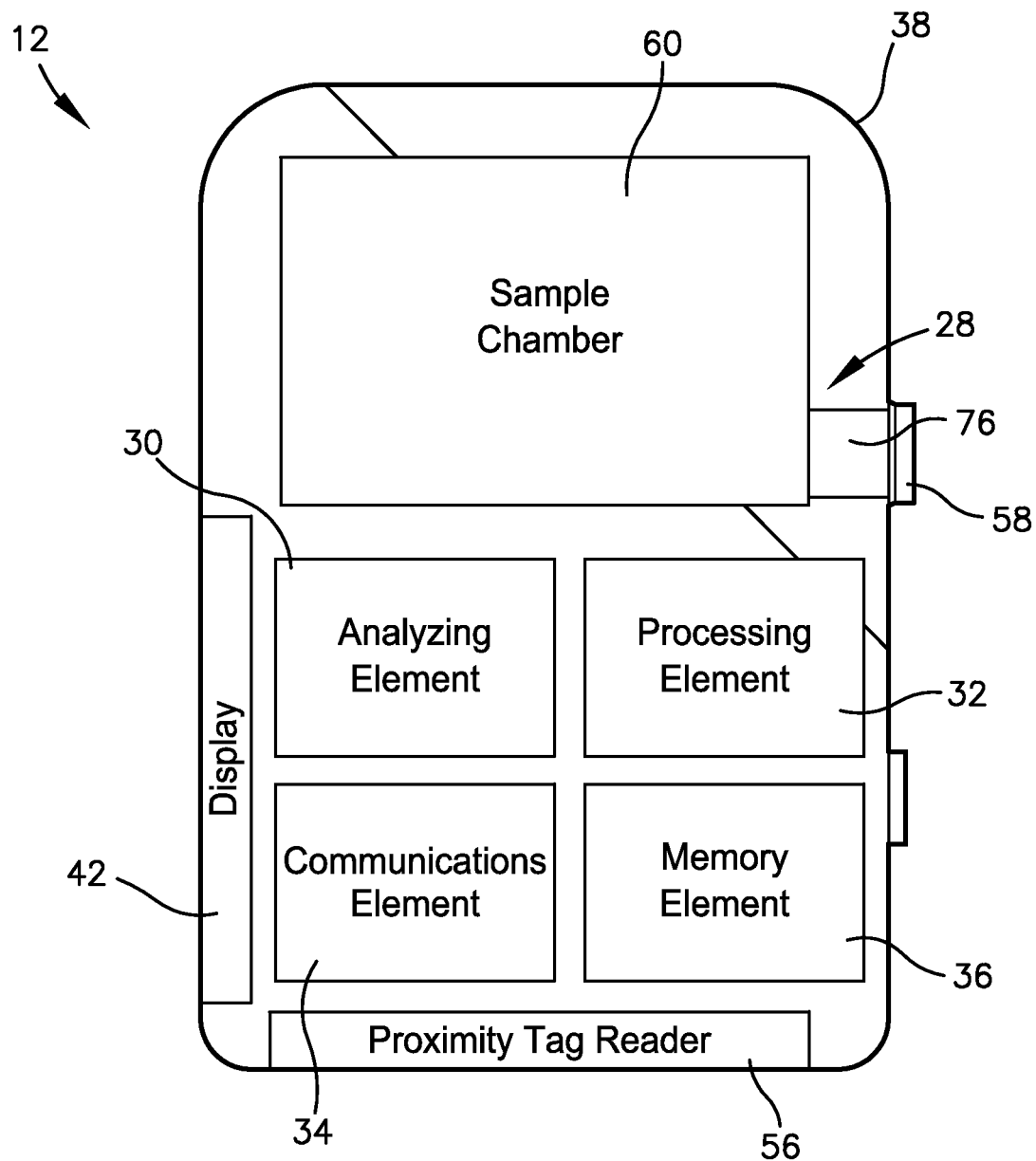
FIG. 5 is a schematic view of the components of the breath analyzer.

The components of the breath analyzer 12 will now be discussed. The breath analyzer 12 comprises the breath receptor 28, the analyzing element 30, at least one processing element 32, at least one memory element 36, the communications element 34, and the housing 38. The breath analyzer 12 may further comprise at least one user input 40, a proximity tag 54, a proximity tag reader 56, at least one status indicator, the display 42, and/or a speaker. A schematic illustration of the components of the breath analyzer 12 can be found in FIG. 5. It should be noted that FIG. 5 is not to scale and presents only a schematic illustration of the components.

The breath receptor 28 comprises a mouthpiece 58 and a sample chamber 60. The mouthpiece 58 is a substantially hollow tube that is at least partially located on the exterior of the breath analyzer 12. The mouthpiece 58 is adapted to receive the donor's mouth and/or nose therearound. As the donor 22 blows into the mouthpiece 58, the mouthpiece 58 directs the flow of breath into the sample chamber 60. The sample chamber 60 is an internal cavity or void in the breath analyzer 12. The sample chamber 60 stores the breath sample for analysis by the analyzing element 30, discussed below.

The breath receptor 28 may have a disposable cover (not illustrated). The disposable cover provides a hygienic covering to the breath receptor 28 so that subsequent donors do not contact bodily fluids of previous donors. The disposable cover is placed over the breath receptor 28 prior to the breath analysis and is then discarded after the breath analysis.

The analyzing element 30 estimates the concentration of alcohol, or other substance, in the blood by analyzing the concentration of alcohol in the breath sample. The analyzing element 30 comprises at least one vial, a set of photocells connected to a meter, and a processing unit to interpret the results (not illustrated). The at least one vial is typically formed of glass or another transparent substance. The vial is filled with a chemical compound. The chemical compound removes the alcohol from the air and reacts with the alcohol to change the color of the solution. The set of photocells detects the degree of color change, which is directly tied to the concentration of alcohol in the breath sample. The processing unit interprets the degree of color change, as detected by the set of photocells, to calculate the breath analysis result. The processing unit may be the processing element 32 of the breath analyzer 12, or it may be separate and communicatively linked.

In another embodiment of the invention, the analyzing element 30 utilizes infrared (IR) spectroscopy to estimate the concentration of alcohol in the breath sample. IR spectroscopy estimates the concentration of alcohol by emitting an IR beam through the sample chamber 60. The IR beam then passes through at least one filter specific to the wavelengths of the bonds of ethanol. A set of photocells detects the amount of IR light passing through the filter. The processing unit then interprets the amount of IR light passing through the filter to calculate the breath analysis result.

The breath analysis result may be displayed on the display 42 of the breath analyzer 12 and/or transmitted to the recording device manager 14, as discussed below. The breath analysis result may be retransmitted by recording device manager to one or more associated devices, such as auxiliary computing device 18, ancillary camera 16, law enforcement vehicle 50, or other component of the system. In alternative embodiments, the breath analysis result is transmitted to the one or more associated devices, such as auxiliary computing device 18, ancillary camera 16, law enforcement vehicle 50, or other component of the system, and without first being transmitted to the recording device manager. Once received by other components of the system, the breath analysis result is used accordingly. For example, the breath analysis result may be stored as metadata associated with the video recording produced by one or more cameras such as ancillary camera 16, displayed on a display of auxiliary computing device 18, a display in law enforcement vehicle 50, or another auxiliary display (such as, for example, a HUD or other body-mounted display worn by law enforcement officer 46). The breath analyzer 12 may announce the breath analysis result via the speaker, and/or give other indications that the breath analysis is complete.

The at least one user input 40 of the breath analyzer 12 may include buttons, knobs, switches, etc. for the input 40 of information by the administrator 44. The user input 40 could include a power button, a start analysis button, a stop analysis button, a reset button, a display toggle button, etc. In the embodiment as shown in FIG. 1, the power button turns the device on and off. In some embodiments, there is no specific start analysis button because the breath analyzer 12 begins the breath analysis automatically upon the input 40 of the breath sample from the donor 22.

The communication element of the breath analyzer 12 transmits information indicative of the breath analysis result to the recording device manager 14. The communication element is communicatively linked to the recording device manager 14, such that messages can be sent therebetween. In some embodiments, the communication element is also communicatively coupled, either directly or indirectly, with one or more other elements of the system. In addition to the breath analysis result, the breath analyzer 12 may transmit information indicative of a status 62. The status 62 could include information such as breath analyzer 12 power on, analysis start time, analysis stop time, current analyzing element reading, analysis successful completion, error detected, error not detected, location of the breath analyzer 12 (for breath analyzers equipped with a location element, discussed below), administrator information (based upon the proximity tag identifier discussed below), date of last breath analyzer testing, data of last breath analyzer calibration, ambient air temperature (as this can affect breath analysis results), one or more identifiers (such as model number or serial number) associated with breath analyzer 12, etc. All of this information can be stored as metadata for video recorded by one or more video cameras such as ancillary video camera 16, or displayed in real time by one or more displays associated with the system, such as that associated with auxiliary computing device 18.

The communications element 34 of the breath analyzer 12 may be wirelessly connected to the recording device manager 14. The communications element 34 may alternatively or in addition be connected via a communications wire to the recording device manager 14 and/or ancillary video camera 16. The communications element 34 transmits the breath analysis result and/or status 62 substantially in real time (as defined below).

The transmission of the breath analysis result to an external location aids in authentication by reducing administrator error in reading the result. The transmission of breath analysis also aids in preservation by storing the data in more than one location. This reduces the likelihood of a loss or destruction of the breath analysis result. The transmission of the breath analysis result also aids in presentation by allowing the breath analysis to be easily and reliably superimposed onto the video from the ancillary video cameras 16 and/or the integral video camera 20 in the breath analyzer 12.

The breath analysis result may be stored in metadata of the recorded video data from the at least one ancillary video camera 16. Metadata associates one set of data with another set of data. The metadata may be embedded in the captured video data, stored externally in a separate file that is associated with the captured video data, otherwise associated with the captured video data, or all of the above. Embedding the breath analysis result into the same file with the captured video data can be advantageous because it allows the metadata to travel as part of the data it describes. In some such embodiments, metadata is associated with a particular frame or frames of the video data. This is advantageous where, for example, the same video file contains more than one breath analysis. In other such embodiments, the metadata is associated with the video file as a whole. Externally stored metadata may also have advantages, such as ease of searching and indexing. The metadata may also be stored in a human-readable format, such that a user can access, understand, and edit the metadata without any special software.

For example, the breath analysis result could be stored in the metadata of the recorded video data of the ancillary video camera 16. A user can subsequently superimpose the breath analysis result by accessing the associated metadata with the recorded video data. The breath analysis result may also have a timestamp that corresponds to the time in which the breath analysis result was communicated to the recording device manager 14. Other information such as the status 62 of the breath analyzer 12 at a certain time may also be added to the metadata of the recorded video data. Some information stored in the metadata may be relatively static, such as a manufacturer name and model of the breath analyzer 12, an identifier assigned to the specific breath analyzer 12 by a law enforcement agency, a date of the last testing and/or calibration of the breath analyzer 12, a name of the last person to perform the testing and/or calibration, etc. The user may also selectively superimpose the status and/or the relatively static information over the recorded video data, as discussed below.

The housing 38 securely contains the analyzing element 30, the communications element 34, and at least a portion of the breath receptor 28. The housing 38 is sized and adapted to fit into a human hand, such that the administrator 44 and/or the donor 22 can hold the breath analyzer 12 during the breath analysis.

Figure 2:
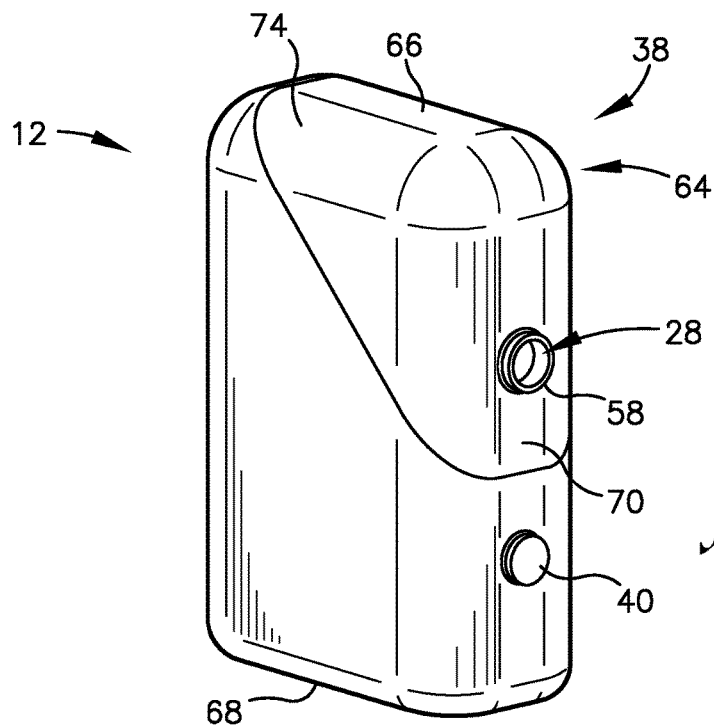
FIG. 2 is a perspective view of a first embodiment of the breath analyzer.
Figure 4:
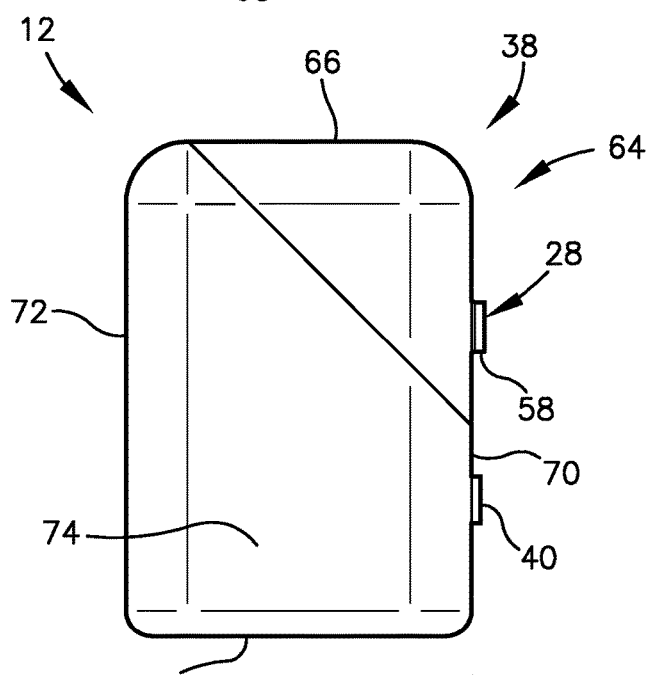
FIG. 4 is a side view of the first embodiment of the breath analyzer.
Figure 3:
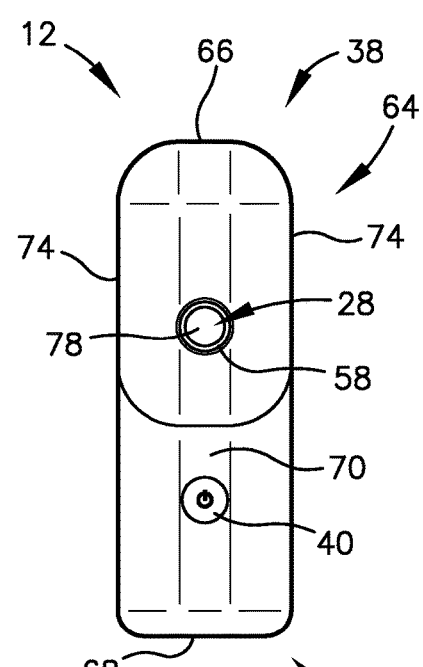
FIG. 3 is a front view of the first embodiment of the breath analyzer.
Figure 7:
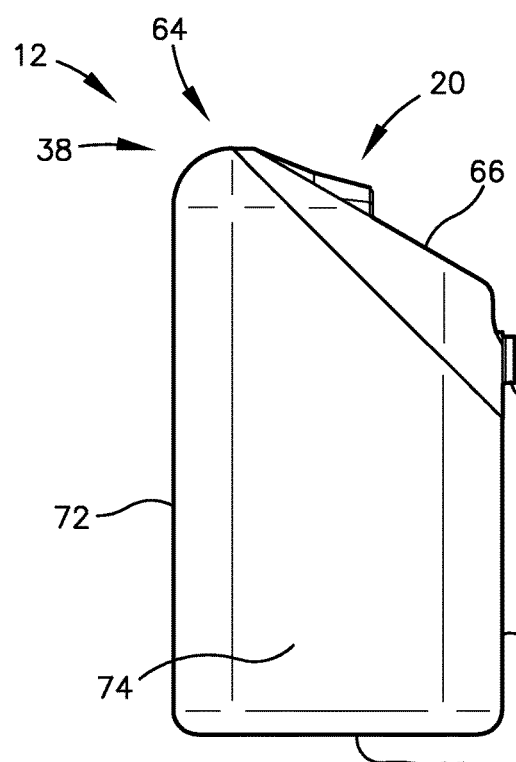
FIG. 7 is a side view of the second embodiment of the breath analyzer.
Figure 6:
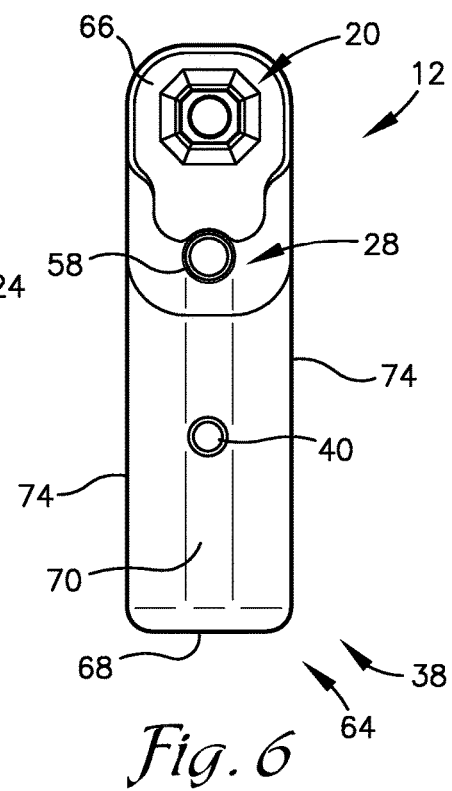
FIG. 6 is a front view of a second embodiment of the breath analyzer with an integral video camera.

The housing 38 is generally a rounded rectangular prism. The housing 38 comprises a main body 64 that presents a top wall 66, a bottom wall 68, a front wall 70, a back wall 72, and two sidewalls 74. The two sidewalls 74 are substantially parallel to each other, and the front wall 70 and back wall 72 are substantially parallel to each other. The top wall 66 and the bottom wall 68 may be substantially parallel, as illustrated in FIGS. 2-4, or the top wall 66 may be at an angle, as illustrated in FIG. 6-7. As illustrated, the transition between the various walls may be rounded or arcuate. The rounded or arcuate transitions provide comfort to a person holding the breath analyzer 12. The main body 64 of the housing 38 could also be another shape, such as substantially a cylinder, substantially an oval cylinder, substantially an ellipsoid, or substantially a sphere.

As shown in FIGS. 2 and 6, the mouthpiece 58 of the breath receptor 28 may be located on the front wall 70 of the housing 38. The mouthpiece 58 may comprise a void 76 or opening into which a disposable mouthpiece cover may be inserted (not illustrated). In other embodiments, the donor 22 exhales directly into the mouthpiece 58 without the use of a disposable mouthpiece cover.

Figure 8:
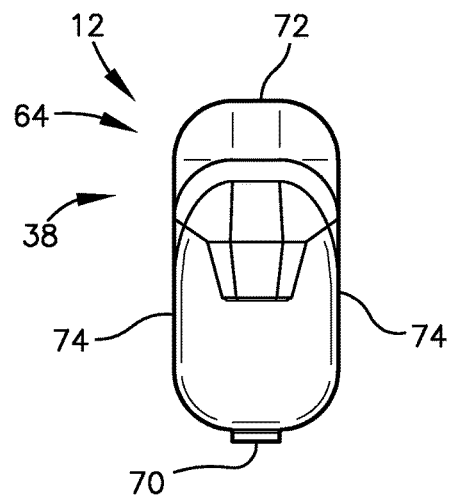
FIG. 8 is a top view of the second embodiment of the breath analyzer.

In embodiments of the invention as illustrated in FIGS. 6-8, the housing 38 may secure the integral video camera 20. The integral video camera 20 records high definition video and pictures of the donor 22 as the breath analysis is being performed. As shown in FIG. 6, the integral video camera 20 may be recessed (i.e., located near the back wall 72) and oriented in a front-facing direction or a diagonally front-upward-facing direction, such that it can observe the donor 22 as the breath analysis is performed. Were the integral video camera 20 placed nearer the front wall 70, the integral video camera 20 may be too close to the donor 22 to capture clear video data. The integral video camera 20 may be activated by the power button, such that the integral video camera 20 is continuously recording while the breath analyzer 12 is powered on. The integral video camera 20 may alternatively be activated by the donor 22 breathing into the breath receptor 28, or by a record start input button. It will be immediate to a person of skill in the art that any functionality described herein with respect to integral video camera 20 is also applicable to ancillary video camera 16, and vice-versa.

Embodiments of the breath analyzer 12 further comprise a location element, such as a GPS receiver (not illustrated). The location element determines and records the GPS location of the breath analyzer 12 during the breath analysis. The location element transmits information indicative of the location to the processing element 32. The location information may then be stored on the memory element 36 of the breath analyzer 12 and/or be transmitted to the recording device manager 14 via the communications element 34. The location element may also determine and record the time of the breath analysis. This information can, like the breath analysis result and other data, be further saved as video metadata, as described above. The location information and time information provide further authentication to the breath analysis result. For example, a criminal defendant would have more difficulty convincing a judge or jury that the breath analysis result was mishandled or confused if the breath analysis result is digitally saved, along with the time and location of the breath analysis that match the time and location of the vehicle stop.

The recording device manager 14 will now be discussed, as illustrated in FIG. 1. The recording device manager 14, such as a Digital Ally® VuLink®, controls and synchronizes various recording devices. For example, the recording device manager 14 links (via wireless communication, wired communication, or both) to the breath analyzer 12, a person-mounted 52 video camera on the law enforcement officer 46, another person-mounted 52 video camera on a second law enforcement officer, a vehicle-mounted 48 video camera in the law enforcement vehicle 50 oriented to observe events external to the law enforcement vehicle 50, a vehicle-mounted 48 video camera in the law enforcement vehicle 50 oriented to observe events internal to the law enforcement vehicle 50, and/or the auxiliary computing device 18 (referred to generically or individually as "the various recording devices"). The recording device manager 14 detects when one video camera begins recording, and then instructs all other associated devices to begin recording. The recording device manager 14 may also send information indicative of a time stamp to the various recording devices for corroborating the recorded data.

For example, the recording device manager 14 may instruct all associated video cameras to begin recording upon the receipt of a signal from the breath analyzer 12 that the breath analysis has begun. This ensures that multiple video cameras record the breath analysis, for future authentication that the breath analysis was performed correctly. The recording device manager 14 may also send a time stamp to all the associated video cameras to provide a corroboration of the various recorded data. Further, the recording device manager 14 may send information indicative of the breath analysis result to each of the video cameras to associate with the recorded video in metadata, to assist in the preservation of the breath analysis result and presentation of the breath analysis result superimposed on the recorded video, and to one or more displays in real time as discussed above to provide quick access to the result to law enforcement personnel.

The recording device manager 14 comprises a processing element, a communications element, and a memory element (not illustrated). The processing element detects the presence of the various recording devices. The processing element receives signals from and generates signals to the various recording devices via the communications element 34.

Figure 9:
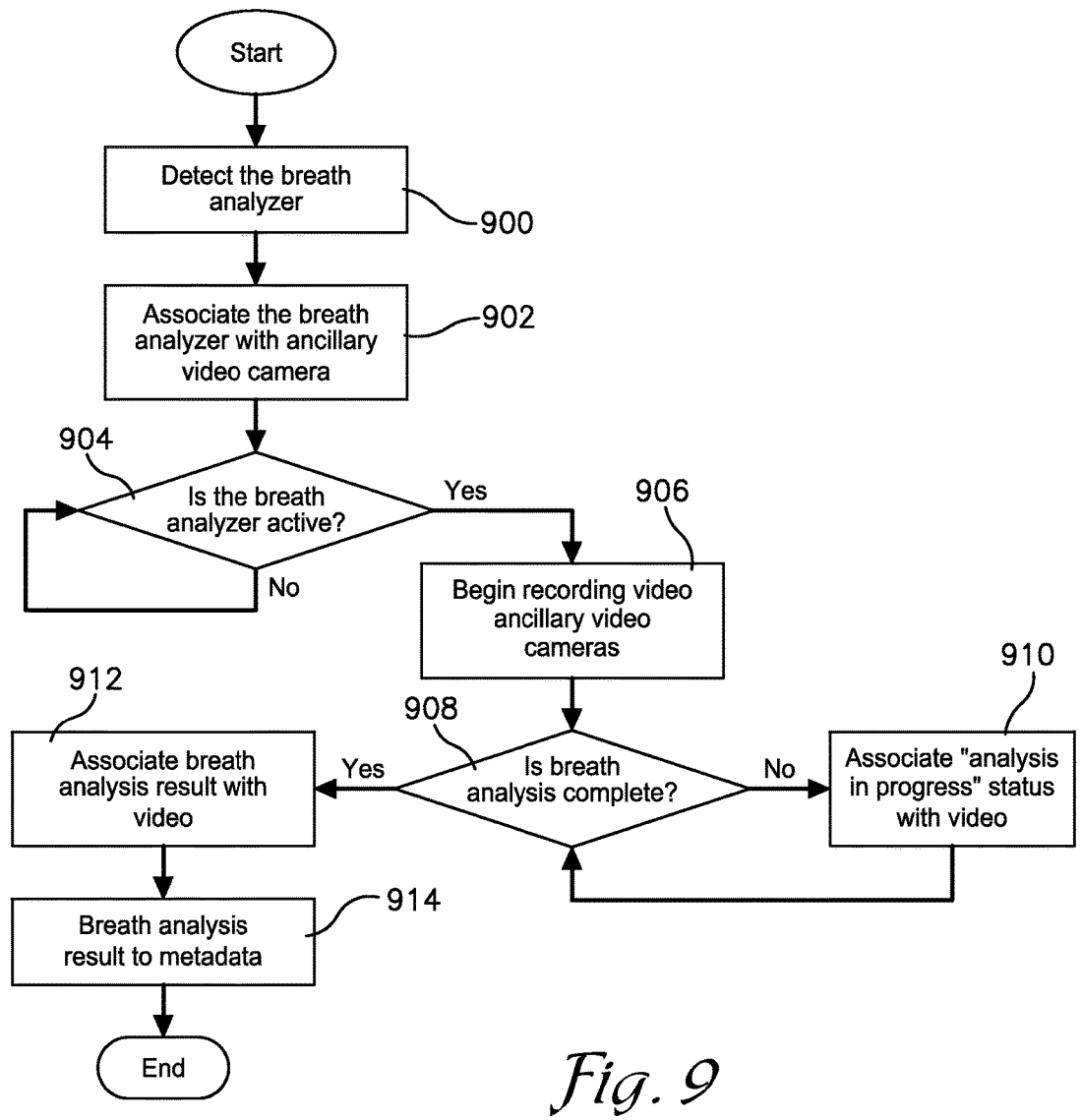
FIG. 9 is a flow diagram illustrating the steps of a method of interacting with the breath analyzer.

An exemplary flow diagram of the interactions between the breath analyzer 12, the recording device manager 14, and the video cameras is illustrated in FIG. 9. The recording device manager 14 begins by attempting to detect the breath analyzer 12, as shown in Step 900. Upon detection, the recording device manager 14 associates the breath analyzer 12 with the other various recording devices by pairing the respective devices, as shown in Step 902. The recording device manager 14 detects if the breath analyzer 12 is active at Step 904. If not, the recording device manager 14 continues to detect the activity of the breath analyzer 12. Upon detecting activity by the breath analyzer 12, the recording device manager 14 instructs the other various recording devices to begin recording if they are not already recording, as shown in Step 906. The recording device manager 14 then detects, at Step 908, whether the breath analyzer 12 has completed the breath analysis. If not, the recording device manager 14 instructs the other various recording devices to associate an "analysis in progress" status 24, 62 with the recorded video, as shown in Step 910. Upon the detection that the breath analysis is complete at Step 912, the recording device manager 14 instructs the other various recording devices to associate the breath analysis result with the recorded video. The recording device manager 14 also saves the breath analysis result to metadata, as shown in Step 914.

Some embodiments of the invention comprise a proximity tag system for authenticating the devices, cameras, and administrators associated with the breath analysis. The proximity tag system comprises a plurality of proximity tags 54 and at least one proximity tag reader 56. Proximity tags are any devices that radiate an identifying signal, herein referred to as the proximity tag identifier, that can be read by a corresponding reader such as the proximity tag reader 56. Proximity tags can be active (meaning that they periodically broadcast their identifier), assisted passive (meaning that they broadcast their identifier only when interrogated by a signal from the reader), or passive (meaning that they have no power source and must be illuminated by a signal from the proximity tag reader 56 in order to radiate their identifier). Other forms of proximity tags are also possible. Proximity tag identifier may be preprogrammed into proximity tags, or may be field-programmable, such that the identifier is assigned by the user when the proximity tag 54 is deployed. One common form of proximity tag system is the radio-frequency identification (RFID) tag and the corresponding RFID reader. Another form of proximity tag system utilizes a challenge-response protocol to avoid the spoofing of a proximity tag identifier.

The proximity tag reader 56 receives the proximity tag identifiers transmitted by proximity tag 54. As depicted, proximity tag reader is integrated into breath analyzer 12, and proximity tag identifiers are then communicated by communications element 34 to the other components of the system. In other embodiments, breath analyzer 12 may instead (or in addition) contain a proximity tag, which is read by another proximity tag reader located in another component of the system such as recording device manager 14. Depending on the type of proximity tag 54, a different type of reader may be required to receive the proximity tag identifiers. For example, an active reader is required to read passive tags. In some embodiments, the proximity tag reader 56 can determine the distance to the transmitting tag based on signal strength or other information. In some embodiments, multiple proximity tag readers are present. In some such implementations, positional information about the tag can be determined based on a relative signal strength at each reader.

The law enforcement officer 46 uses a proximity tag 54 that contains a proximity tag indicator specific to that law enforcement officer 46 to authenticate the name, unit, and/or status of the specific law enforcement officer 46 using the recording device manager 14 and/or the breath analyzer 12. The proximity tag 54 may be located within a proximity card held by the officer, within the badge worn by the officer, on a watch or a belt worn by the officer, etc. There may also be a proximity tag 54 in the breath analyzer 12 and/or the ancillary video cameras 16. The proximity tag reader 56 reduces work to be performed at a later time to associate the recorded video data and breath analysis result with the specific law enforcement officer 46.

Some embodiments of the invention comprise the auxiliary computing device 18 that is associated with the recording device manager 14. The auxiliary computing device 18 records the video data and statuses of the ancillary video cameras 16, the breath analysis results and status 62 from the breath analyzer 12, etc. For example, the auxiliary computing device 18 could be a laptop computer within the law enforcement vehicle 50, as illustrated in FIG. 1. As another example, the auxiliary computing device 18 could be a digital video recorder that is a stand-alone device located within the law enforcement vehicle 50 and associated with the recording device manager. As yet another example, the auxiliary computing device 18 is within and associated with the recording device manager 14. In other embodiments, the auxiliary computing device 18 is within and associated with the ancillary video cameras 16. As such, the ancillary video cameras 16 each record their video data on their own internal memory elements with associated metadata such as the breath analysis result. In still other embodiments, the system 10 uses a combination of the above-mentioned recording methods for redundant data storage and/or to allow different types of devices to store data in different ways.

In embodiments, the breath analysis result is saved to metadata associated with the video at a specific time stamp or time stamps. Then, during the preparation for a hearing, the breath analysis result can be selectively superimposed on the video by a user. The breath analysis result may be automatically superimposed on the video by default, and present the user with the option to remove the breath analysis result from the video. In some jurisdictions, the breath analysis result may be inadmissible in court, or may only be admissible for certain purposes (such as the establishment of probable cause for the arrest, but not as evidence of intoxication). For this reason, the user may desire to have the breath analysis result superimposed, to not have the breath analysis superimposed, or to have two separate videos (one superimposed, the other not). Saving the breath analysis result to metadata provides this benefit. In other embodiments, the breath analysis result is directly and permanently superimposed on the video.

Various methods of embodiments of the invention will now be discussed. A non-transitory computer readable storage medium having a computer program stored thereon may instruct the at least one processing element to implement the steps of at least one of the described methods. The non-transitory computer readable storage medium may be located within the housing 38 of the breath analyzer 12, within the recording device manager 14, within the auxiliary computing device 18, within the at least one ancillary video camera 16, within a computing device secured within the law enforcement vehicle 50, and/or within a generic computing device.

Figure 10:
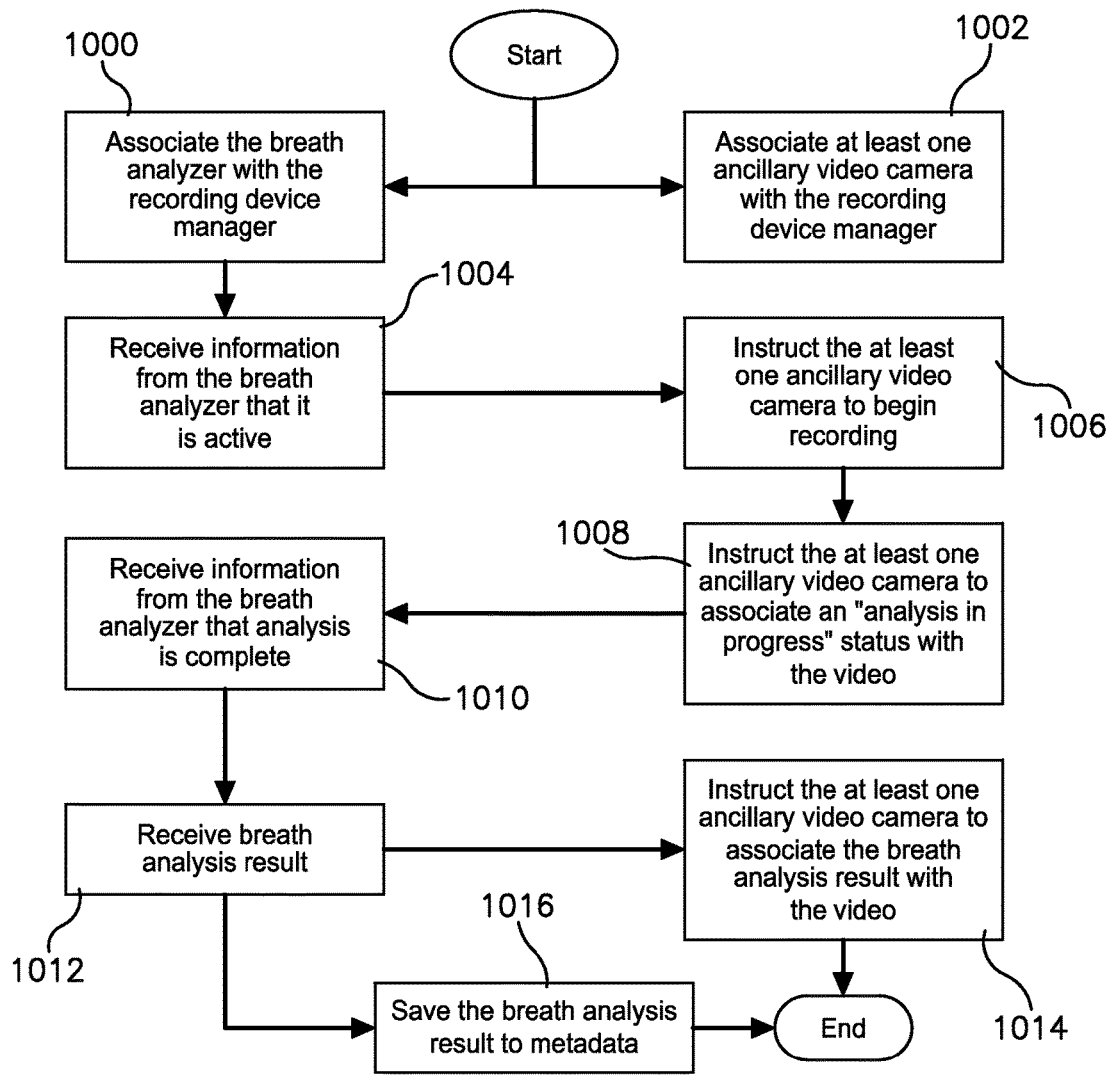
FIG. 10 is a flow diagram illustrating the steps of a first method of authenticating and preserving the breath analysis result.

A method of authenticating and preserving breath analysis results is illustrated in FIG. 10. In Step 1000, the breath analyzer 12 is associated with the recording device manager 14. In Step 1002, at least one ancillary video camera 16 is associated with the recording device manager 14. In Step 1004, the recording device manager 14 receives information indicative that the breath analyzer 12 is active. The recording device manager 14 then instructs the at least one ancillary video camera 16 to begin recording (if it is not already) in Step 1006. The recording device manager 14 in Step 1008 also instructs the at least one ancillary video camera 16 to associate an "analysis in progress" status 24, 62 with the video being recorded. At this step, additional information may also be associated with the video being recorded. Such information can include information relating to the breath analyzer (as discussed above), information relating to the scene (such as any proximity tags detected by proximity tag reader 56), or other information (such as the identities of any other ancillary or integrated video cameras currently recording the scene). In Step 1010, the recording device manager 14 receives information indicative that the breath analysis is complete. In Step 1012, the recording device manager 14 receives information indicative of the breath analysis result. Then, the recording device manager 14 instructs the at least one ancillary video camera 16 to associate the breath analysis result with the video being recorded in Step 1014. In some embodiments, the breath analysis is additionally communicated to one or more other components of the system for processing, storage, or display. The recording device manager also saves the breath analysis result to metadata in Step 1016. Some embodiments of the method of authenticating and preserving breath analysis data further comprise the following steps: receiving information indicative of a proximity tag identifier of a proximity tag 54 being within the range of the proximity tag reader 56; associating proximity tag identifier with the video data being recording; and associating the proximity tag identifier with the breath analysis results.

Figure 11:
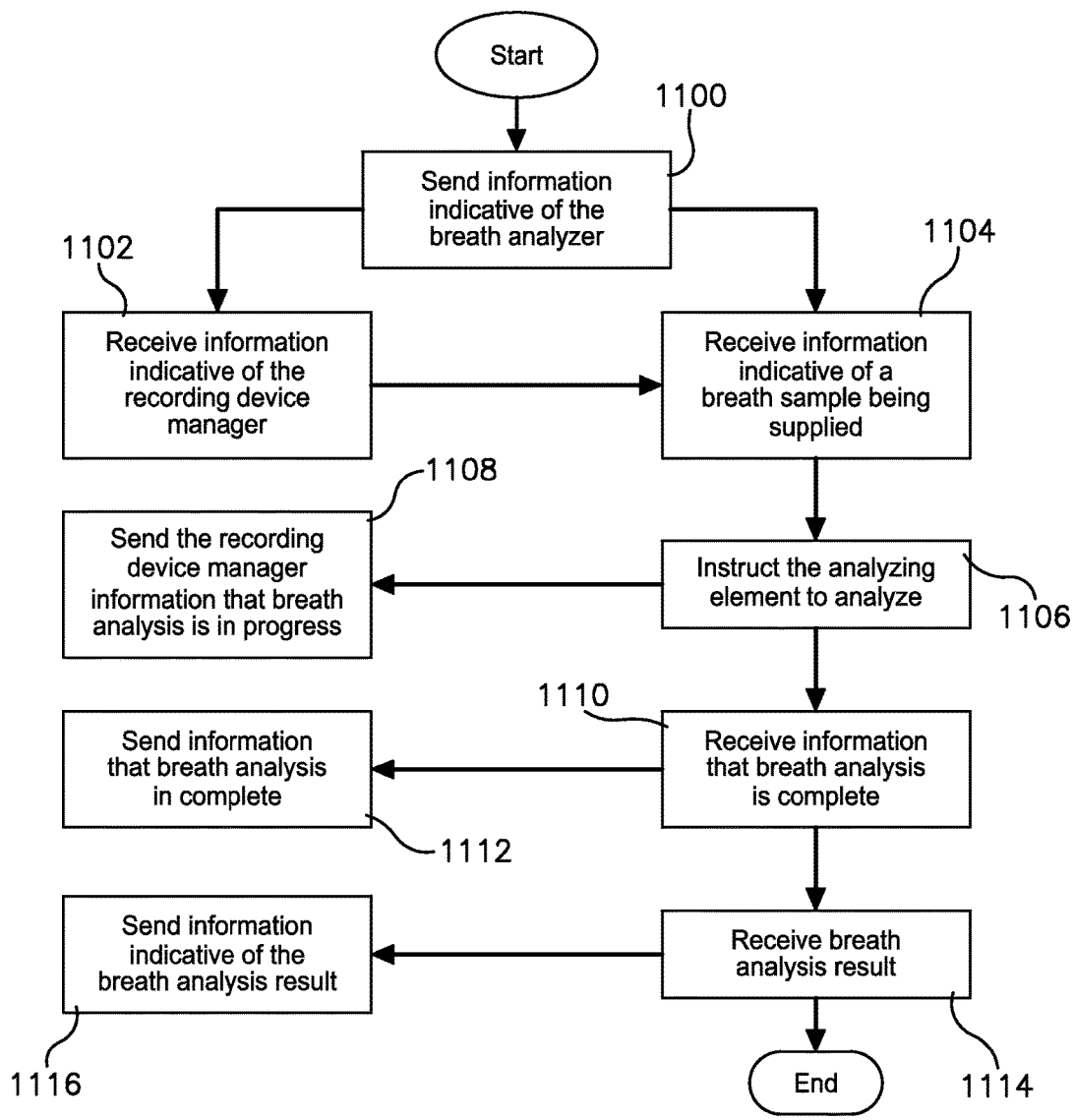
FIG. 11 is a flow diagram illustrating the steps of a second method of authenticating and preserving the breath analysis result.

Another method of authenticating and preserving breath analysis results is illustrated in FIG. 11. The breath analyzer 12 sends a set of information indicative of the breath analyzer 12 in Step 1100. The breath analyzer 12 also receives information indicative of a recording device manager 14 in Step 1102. The breath analyzer 12 then receives information indicative of the breath sample being supplied to the breath receptor 28 in Step 1104. The breath analyzer 12 then, in Step 1106, instructs the analyzing element 30 to analyze the breath sample. The breath analyzer 12 then sends to the recording device manager 14 a set of information indicative that the analyzing element 30 has begun analyzing in Step 1108. The breath analyzer 12 receives information indicative of the analyzing element 30 completing the breath analysis in Step 1110. Then, in Step 1112, the breath analyzer 12 sends, to the recording device manager 14, a set of information indicative that the breath analysis is complete. In Step 1114, the breath analyzer 12 receives, from the analyzing element 30, a breath analysis result. Finally, in Step 1114, the breath analyzer 12 sends, to the recording device manager 14, information indicative of the breath analysis result. Some embodiments further comprise the step of storing the breath analysis result in the memory element 36 and/or displaying it on one or more local or remote displays. Some embodiments further comprise the steps of receiving, from the recording device manager 14, information indicative of the time and/or location; and associating the information indicative of the time and/or location with the breath analysis results. Some embodiments further comprise the following steps: receiving information indicative of a proximity tag identifier from the recording device manager 14; associating the proximity tag identifier with the breath analysis results.

Figure 12:
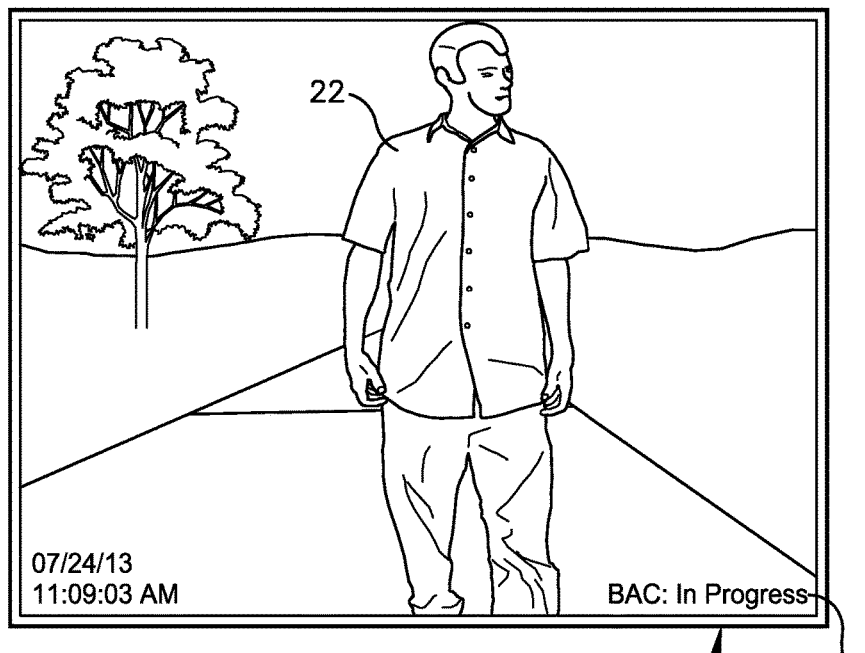
FIG. 12 is an exemplary video capture frame showing a breath analyzer status superimposed thereon.
Figure 13:
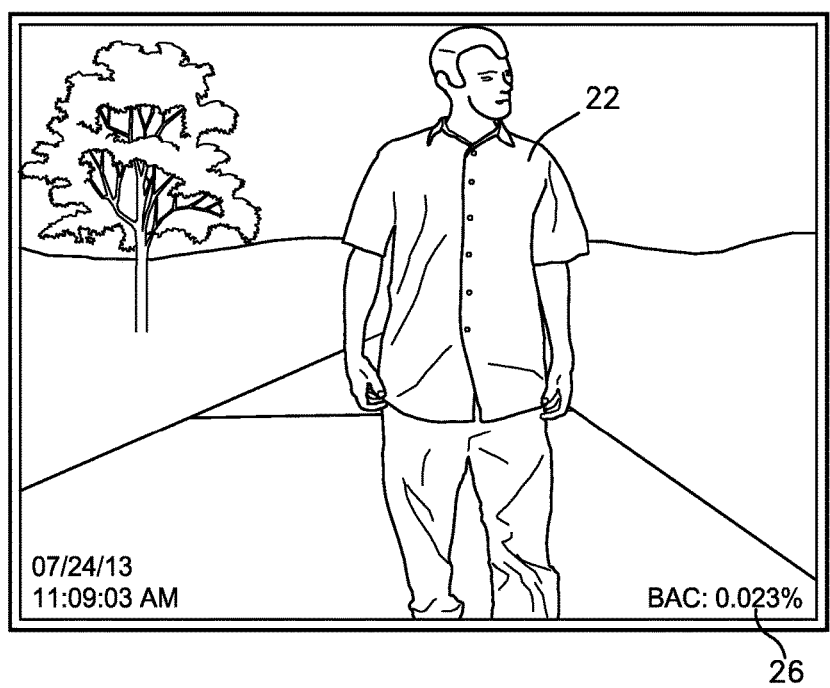
FIG. 13 is another exemplary video capture frame showing a breath analysis result superimposed thereon.
Figure 14:
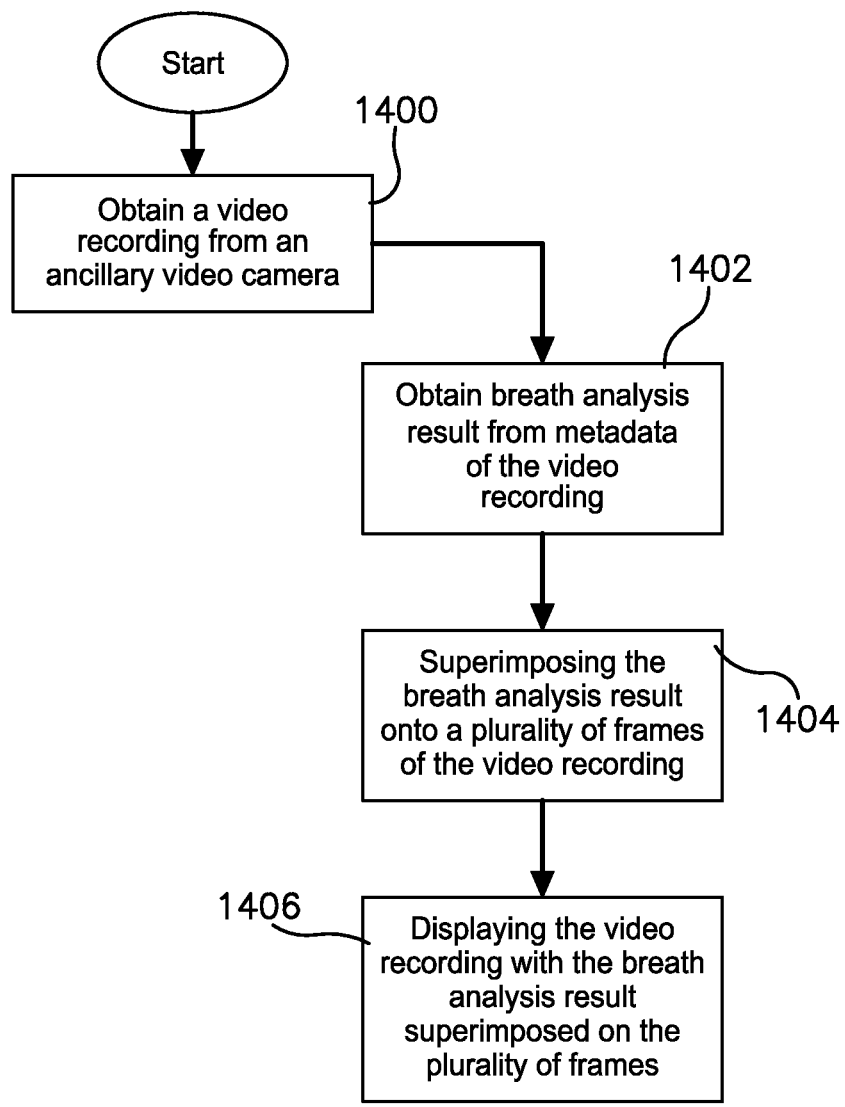
FIG. 14 is a flow diagram illustrating the steps of a method of presenting the breath analysis result.

Two exemplary presentations of the breath analysis data are illustrated in FIGS. 12 and 13. A method of presenting breath analysis results is illustrated in FIG. 14. The steps comprise obtaining a video recording from an ancillary video camera 16, in Step 1400; obtaining information indicative of the breath analysis result from the metadata associated with a video recording, in Step 1402; superimposing the breath analysis result onto a plurality of frames of the video recording, such that the breath analysis result is superimposed on frames of the video recording at a time approximately the same as, and for a certain period of time following, the time in which the recording device manager 14 received the information indicative of the breath analysis result, in Step 1404; and displaying the video recording with the breath analysis result superimposed on the plurality of frames, in Step 1406. Other embodiments of the method comprise the steps of obtaining information indicative of the status 62 of the breath analyzer 12 from the metadata associated with the video recording; superimposing the status 62 of the breath analyzer 12 onto the video recording; and synchronizing the superimposition such that the status 62 of the breath analyzer 12 is displayed at the time corresponding with the status 62. Other embodiments of the method comprise the steps of obtaining information indicative of the administrator 44 from the metadata associated with the video recording; and superimposing the information indicative of the administrator 44 onto the video recording. The superimposed information may change with subsequent frames of the video recording. For example, a series of frames may show the "analysis in progress" reading 24 (as illustrated in FIG. 12) followed by a series of frames showing the breath analysis result (as illustrated in FIG. 13). It will be immediately apparent to a person of skill in the art that any of the information gathered by or stored in the system can be superimposed on, or associated as metadata with, the video recording. Information can be displayed individually, in combination, alternation, or simultaneously.

The computer program of embodiments of the invention comprises a plurality of code segments executable by a computing device for performing the steps of various methods of the invention. The steps of the method may be performed in the order discussed, or they may be performed in a different order, unless otherwise expressly stated. Furthermore, some steps may be performed concurrently as opposed to sequentially. Also, some steps may be optional. The computer program may also execute additional steps not described herein. The computer program, system 10, and method of embodiments of the invention may be implemented in hardware, software, firmware, or combinations thereof, which broadly comprises server devices, computing devices, and a communications network.

The computer program of embodiments of the invention may be responsive to user input. As defined herein user input may be received from a variety of computing devices including but not limited to the following: desktops, laptops, calculators, telephones, smartphones, smart watches, in-car computers, camera systems, or tablets. The computing devices may receive user input from a variety of sources including but not limited to the following: keyboards, keypads, mice, trackpads, trackballs, pen-input devices, printers, scanners, facsimile, touchscreens, network transmissions, verbal/vocal commands, gestures, button presses or the like.

The server devices and computing devices may include any device, component, or equipment with a processing element and associated memory elements. The processing element may implement operating systems, and may be capable of executing the computer program, which is also generally known as instructions, commands, software code, executables, applications ("apps"), and the like. The processing element may include processors, microprocessors, microcontrollers, field programmable gate arrays, and the like, or combinations thereof. The memory elements may be capable of storing or retaining the computer program and may also store data, typically binary data, including text, databases, graphics, audio, video, combinations thereof, and the like. The memory elements may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), and the like, or combinations thereof. In addition to these memory elements, the server devices may further include file stores comprising a plurality of hard disk drives, network attached storage, or a separate storage network.

The computing devices may specifically include mobile communication devices (including wireless devices), work stations, desktop computers, laptop computers, palmtop computers, tablet computers, portable digital assistants (PDA), smart phones, and the like, or combinations thereof. Various embodiments of the computing device may also include voice communication devices, such as cell phones and/or smart phones. In preferred embodiments, the computing device will have an electronic display operable to display visual graphics, images, text, etc. In certain embodiments, the computer program facilitates interaction and communication through a graphical user interface (GUI) that is displayed via the electronic display. The GUI enables the user to interact with the electronic display by touching or pointing at display areas to provide information to the system 10.

The communications network may be wired or wireless and may include servers, routers, switches, wireless receivers and transmitters, and the like, as well as electrically conductive cables or optical cables. The communications network may also include local, metro, or wide area networks, as well as the Internet, or other cloud networks. Furthermore, the communications network may include cellular or mobile phone networks, as well as landline phone networks, public switched telephone networks, fiber optic networks, or the like.

The computer program may run on computing devices or, alternatively, may run on one or more server devices. In certain embodiments of the invention, the computer program may be embodied in a stand-alone computer program (i.e., an "app") downloaded on a user's computing device or in a web-accessible program that is accessible by the user's computing device via the communications network. As used herein, the stand-along computer program or web-accessible program provides users with access to an electronic resource from which the users can interact with various embodiments of the invention.

Execution of the computer program of embodiments of the invention performs steps of the method of embodiments of the invention. Because multiple users may be updating information stored, displayed, and acted upon by the computer program, information displayed by the computer program is displayed in real-time. "Real-time" as defined herein is when the processing element of the system 10 performs the steps less than every 1 second, every 500 milliseconds, every 100 milliseconds, or every 16 milliseconds.

The law enforcement field is growing more dependent on recording devices such as cameras and audio recorders to preserve evidence. Officers now use dash-cams, hidden cameras, and personal recording devices worn by the officers to obtain crucial video and audio data recordings. However, managing these devices and corroborating the recorded data remains difficult and problematic. For example, recording devices often use different cues to start recording, or require manual operation, which can result in the devices failing to record at a crucial time. Manually managing recording devices can be distracting to the officer, which is particularly undesirable in dangerous situations. Another problem is that in a court of law, evidence is bolstered if corroborated or otherwise forensically verifiable, but multiple recordings may be difficult to corroborate based solely on their content. Additionally, correlating and organizing evidence is time consuming and increases the workload of often understaffed law enforcement departments.

An embodiment of a multiple recording device management system (hereinafter "management system") includes an intermediate multiple recording device managing apparatus (hereinafter "recording device manager" or "manager"), a vehicle recording device mounted in a police vehicle and communicatively coupled (i.e., synced) to the recording device manager, and a personal recording device carried by a police officer and wirelessly synced to the recording device manager. The recording device manager is operable to detect when the vehicle recording device, personal recording device, or any other synced device in range has started recording and to broadcast or transmit a signal to any synced recording device in range instructing recording by the respective device. The recording device manager also may generate time stamps and unique serial numbers for a data recording, and create or collect metadata and transmit such time stamps, unique serial number, and metadata to the recording devices, for corroborating the recorded data. For illustrative purposes, the management system includes the vehicle recording device and the personal recording device, but it will be understood that duplicate or additional devices, such as audio recorders, thermal imagers, security cameras, radios, seismic sensors, radar and LIDAR scanners, and chemical analyzers, can be synced to the recording device manager. Moreover, multiple personal recording devices can be synced with the manager, as described below.

In one embodiment, power is supplied to the components of the video system from the vehicle. Some embodiments may have a weatherproofed power button exposed on the housing. The power provided is heavily filtered and regulated to avoid interference. The video system, using the particular components described herein, may require 4 amps from a 10 V to 24 V DC power supply. The video system may include a cable that is configured to plug into the power input connector of the console housing and into a standard vehicle power jack, such as a "cigarette lighter" type power jack. It should be noted that the illustrated embodiment of the invention does not include an internal power source. However, some embodiments of the system may include an internal power source, such as a battery. Additionally, the system may be provided with a "stealth" mode in which the camera and the microphone are active and recording, but the lights and indicators, such as the one or more LEDs, are turned off, thereby making the system appear to be dormant. Furthermore, the system may provide "pre-event" recording in which the system records constantly in a loop of a selected duration of time, such as thirty seconds or sixty seconds, so that when an event triggers recording, the events occurring shortly prior to the initiation of recording are also recorded and stored.

An embodiment of the present invention is a digital video recording system broadly comprising a camera component, a recording component, and a mounting assembly. The digital video recording system is portable and relatively small, such that the system can be easily carried by a user on the user's body, a clothing article of the user, a device carried by the user, such as a firearm, or in a vehicle. The system is unobtrusive and lightweight so as to not interfere with routine activity by the user. Moreover, the mounting assembly of the system for mounting on the user's body or clothing article of the user provides a secure mount that will not become dislodged, even under active movement by the user.

An exemplary scenario of the management system in use is now described for illustrative purposes. The management system may be used by the police officer to record video data during a traffic stop. The recording device manager may be mounted near the vehicle recording device, such as on the windshield of the police vehicle. Alternatively, the recording device manager may be mounted anywhere within the police vehicle that allows for the recording device manager to communicate (either via a wired or wireless connection) with the vehicle recording device or a recording device manager (not shown). In exemplary embodiments, the vehicle recording device is aimed forwards to record the traffic stop, and the personal recording device is mounted to the police officer's person or is otherwise carried by the police officer, such as on a lanyard.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for administering a breath analysis to a donor, the system comprising:
   at least one video recorder including an input for capturing video data, a video recorder processor, a video recorder receiver, a video recorder transmitter, and a memory for storing the captured video data;
   a recording device manager communicatively coupled with the at least one video recorder, said recording device manager including a transmitter for transmitting one or more signals, a receiver for receiving one or more signals, and a recording device manager processor;
   a breath analyzer communicatively coupled with the recording device manager,
   said breath analyzer including a transmitter for transmitting one or more signals and a breath analyzer processor; and
   at least one non-transitory computer storage medium storing computer-executable instructions that, when executed by one or more of the video recorder processor, recording device manager processor, and breath analyzer processor, cause the one or more processors to perform the following steps:
   performing, by the breath analyzer, a breath analysis of the donor;
   obtaining, by the breath analyzer, a breath analysis result;
   receiving, by the recording device manager and from the breath analyzer, information indicative of a start of the breath analysis;
   in response to receiving the information indicative of the start of the breath analysis, transmitting, by the recording device manager and to the at least one video recorder, a signal causing the at least one video recorder to preserve the video data captured by the at least one video recorder during the breath analysis of the donor;
   receiving, by the recording device manager and from the breath analyzer, the breath analysis result; and
   storing the breath analysis result with the preserved video data.

2. The system of claim 1, wherein the breath analyzer includes a breath analyzer housing and a video camera housed in the breath analyzer housing.

3. The system of claim 1,
   wherein the at least one video recorder is a first video recorder, the input is a first input for capturing first video data, the video recorder processor is a first video recorder processor, the video recorder transmitter is a first video recorder transmitter, and the memory is a first memory for storing the captured first video data,
   wherein the signal transmitted by the recording device manager and to the first video recorder is a first signal,
   wherein the preserved video data is a first preserved video data,
   said system further including a second video recorder including a second input for capturing second video data, a second video recorder processor, a second video recorder transmitter, and a second memory for storing the captured second video data, and
   wherein said at least one non-transitory computer storage medium storing computer-executable instructions causes the one or more processors, upon execution, to perform the following steps:
   in response to receiving the information indicative of the start of the breath analysis, transmitting, by the recording device manager and to the second video recorder, a second signal causing the second video recorder to preserve the second video data captured by the second video recorder during the breath analysis of the donor; and
   associating the breath analysis result with the preserved second video data.

4. The system of claim 3, wherein one or more of the first video recorder and the second video recorder is configured to be mounted in a vehicle.

5. The system of claim 3, wherein at least one of the first video recorder processor and the second video recorder processor is programmed to implement pre-event recording.

6. The system of claim 5,
   wherein the recording device manager includes a recording device manager housing,
   wherein the first video recorder includes a first video recorder housing, and wherein the second video recorder includes a second video recorder housing, each of said recording device manager housing, said first video recorder housing, and said second video recorder housing being distinct and separate housings.

7. The system of claim 6, wherein at least one of the first video recorder and the second video recorder is configured for mounting on a person's body or article of clothing worn by the person.

8. The system of claim 7, wherein the breath analyzer includes a global positioning system (GPS) receiver for determining a location of the breath analyzer.

9. The system of claim 8, wherein said at least one non-transitory computer storage medium storing computer-executable instructions causes the one or more processors, upon execution, to perform the following step:

transmitting, by the recording device manager and to one or more of the first and second video recorders, the breath analysis result.

10. The system of claim 9, wherein the step of associating the breath analysis result with the preserved first video data includes the step of:

including the breath analysis result in metadata for the preserved first video data; and wherein the step of associating the breath analysis result with the preserved second video data includes the step of:

including the breath analysis result in metadata for the preserved second video data.

11. The system of claim 10, wherein said at least one non-transitory computer storage medium storing computer-executable instructions causes the one or more processors, upon execution, to perform the following step:

transmitting to an auxiliary computer the preserved first video data, the preserved second video data, and the breath analysis result.

12. The system of claim 11, wherein said at least one non-transitory computer storage medium storing computer-executable instructions causes the one or more processors, upon execution, to perform the following steps:

receiving, by the recording device manager and from the breath analyzer, a status of the breath analyzer; and associating the status of the breath analyzer with one or more of the preserved first video data and the preserved second video data, wherein the status of the breath analyzer is selected from the group consisting of: the breath analyzer power on, breath analysis start time, breath analysis stop time, detection of an error associated with the breath analyzer, and location of the breath analyzer.

13. At least one non-transitory computer storage medium storing computer-executable instructions that, when executed by a processor, cause the processor to perform the following steps:

receiving, by a recording device manager including a transmitter and a receiver, and from a breath analyzer, information indicative of a start of a breath analysis of a donor;

in response to receiving the information indicative of the start of the breath analysis, transmitting a signal, by the recording device manager and to a communicatively coupled video recorder including a video recorder receiver and a video recorder transmitter, that causes the video recorder to preserve video data captured by the video recorder during the breath analysis of the donor;

receiving, by the recording device manager and from the breath analyzer, the breath analysis result; and storing the breath analysis result with the preserved video data.

14. The at least one non-transitory computer storage medium of claim 13, wherein the video recorder is a first video recorder, wherein the signal transmitted by the recording device manager and to the first video recorder is a first signal, wherein the preserved video data is a first preserved video data, and wherein said at least one non-transitory computer storage medium storing computer-executable instructions causes the processor, upon execution, to perform the following steps:

in response to receiving the information indicative of the start of the breath analysis, transmitting, by the recording device manager and to a communicatively coupled second video recorder including a second video recorder receiver and a second video recorder transmitter, a second signal that causes the second video recorder to preserve video data captured by the second video recorder during the breath analysis of the donor; and associating the breath analysis result with the preserved second video data.

15. The at least one non-transitory computer storage medium of claim 14, wherein said at least one non-transitory computer storage medium storing computer-executable instructions causes the processor, upon execution, to perform the following step:

transmitting, by the recording device manager and to one or more of the first and second video recorders, the breath analysis result;

wherein the step of associating the breath analysis result with the preserved first video data includes the step of:

including the breath analysis result in metadata for the preserved first video data; and wherein the step of associating the breath analysis result with the preserved second video data includes the step of:

including the breath analysis result in metadata for the preserved second video data.

16. The at least one non-transitory computer storage medium of claim 15, wherein said at least one non-transitory computer storage medium storing computer-executable instructions causes the processor, upon execution, to perform the following step:

transmitting to an auxiliary computer the preserved first video data, the preserved second video data, and the breath analysis result.

17. The at least one non-transitory computer storage medium of claim 15, wherein said at least one non-transitory computer storage medium storing computer-executable instructions causes the processor, upon execution, to perform the following steps:

receiving, by the recording device manager and from the breath analyzer, a status of the breath analyzer; and associating the status of the breath analyzer with one or more of the preserved first video data and the preserved second video data,
wherein the status of the breath analyzer is selected from the group consisting of: the breath analyzer power on, breath analysis start time, breath analysis stop time, detection of an error associated with the breath analyzer, and location of the breath analyzer.

18. A method for administering a breath analysis to a donor, the method comprising the steps of:
receiving, by a recording device manager including a transmitter and a receiver, and from a breath analyzer, information indicative of a start of a breath analysis of a donor;
in response to receiving the information indicative of the start of the breath analysis, transmitting a first signal, by the recording device manager and to a communicatively coupled first video recorder including a first video recorder receiver and a first video recorder transmitter, that causes the first video recorder to preserve first video data captured by the first video recorder during the breath analysis of the donor;
in response to receiving the information indicative of the start of the breath analysis, transmitting a second signal, by the recording device manager and to a communicatively coupled second video recorder including a second video recorder receiver and a second video recorder transmitter, that causes the second video recorder to preserve second video data captured by the second video recorder during the breath analysis of the donor;
receiving, by the recording device manager and from the breath analyzer, the breath analysis result; and
storing the breath analysis result with the preserved first video data and the preserved second video data.

19. The method of claim 18, wherein the step of associating is performed by the recording device manager.

20. The method of claim 18, further including the step of:
transmitting the breath analysis result, the preserved first video data, and the preserved second video data to an auxiliary computer distinct from the recording device manager,
wherein the step of associating the breath analysis result with the preserved first video data and the preserved second video data is performed by the auxiliary computer.

21. The method of claim 18, further including the step of:
compositing the breath analysis result with one or more of the preserved first video data and the preserved second video data and at least one of the breath analysis result, a time and date associated with the breath analysis, the donor's name, a law enforcement officer administering the breath analysis, or a location of the breath analysis,
such that the breath analysis result is viewable, on an electronic user interface, with the composited one or more of the preserved first and second video data.

22. The method of claim 18, further including the step of:
transmitting, by the recording device manager and to both the first and second video recorders, the breath analysis result;
wherein the step of associating the breath analysis result with the preserved first video data includes the step of:
including the breath analysis result in metadata for the preserved first video data; and
wherein the step of associating the breath analysis result with the preserved second video data includes the step of:
including the breath analysis result in metadata for the preserved second video data.

23. The method of claim 18, further including the steps of:
receiving, by the recording device manager and from the breath analyzer, a status of the breath analyzer; and
associating the status of the breath analyzer with one or more of the preserved first video data and the preserved second video data,
wherein the status of the breath analyzer is selected from the group consisting of: the breath analyzer power on, breath analysis start time, breath analysis stop time, detection of an error associated with the breath analyzer, and location of the breath analyzer.

* * * * *